(12) United States Patent
Ezeamuzie et al.

(10) Patent No.: US 11,608,320 B2
(45) Date of Patent: Mar. 21, 2023

(54) OXAZOLIDINONE HYDROXAMIC ACID DERIVATIVES

(71) Applicant: KUWAIT UNIVERSITY, Safat (KW)

(72) Inventors: Charles Ifeamalume Ezeamuzie, Safat (KW); Oludotun Adebayo Phillips, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 139 days.

(21) Appl. No.: 17/145,357

(22) Filed: Jan. 10, 2021

(65) Prior Publication Data

US 2021/0238151 A1 Aug. 5, 2021

Related U.S. Application Data

(60) Provisional application No. 62/969,120, filed on Feb. 2, 2020.

(51) Int. Cl.
| | | |
|---|---|---|
| C07D 263/06 | (2006.01) | |
| A61P 11/06 | (2006.01) | |
| A61P 37/08 | (2006.01) | |
| A61K 31/421 | (2006.01) | |

(52) U.S. Cl.
CPC .......... *C07D 263/06* (2013.01); *A61K 31/421* (2013.01); *A61P 11/06* (2018.01); *A61P 37/08* (2018.01)

(58) Field of Classification Search
CPC ........ A61K 31/421; A61P 11/06; A61P 37/08; C07D 263/06
See application file for complete search history.

(56) References Cited

U.S. PATENT DOCUMENTS

| | | |
|---|---|---|
| 5,036,067 A | 7/1991 | Girard et al. |
| 5,164,510 A | 11/1992 | Brickner |
| 5,792,883 A | 8/1998 | Harada et al. |
| 6,277,985 B1 | 8/2001 | Gadwood et al. |
| 6,998,420 B2 | 2/2006 | Perrault et al. |
| 7,157,456 B2 | 1/2007 | Straub et al. |
| 7,691,889 B2 | 4/2010 | Arora et al. |
| 7,767,702 B2 | 8/2010 | Straub et al. |
| 8,273,745 B2 | 9/2012 | Terasaka et al. |
| 2008/0139563 A1 | 6/2008 | Tung et al. |
| 2008/0306070 A1 | 12/2008 | Perzborn et al. |
| 2010/0120718 A1 | 5/2010 | Perzborn |
| 2010/0160301 A1 | 6/2010 | Perzborn et al. |
| 2016/0024011 A1 | 1/2016 | Zeidan et al. |

FOREIGN PATENT DOCUMENTS

| | | |
|---|---|---|
| EP | 1304107 A2 | 4/2003 |
| WO | WO0119366 A1 | 3/2001 |

OTHER PUBLICATIONS

Phillips et al., "Synthesis and biological evaluation of novel 5-(hydroxamic acid)methyl oxazolidinone derivatives," Eur. J. Med. Chem. 2015;106:120-31. PMID: 26536532. (Year: 2015).*
Hedaya et al., "Antiproliferative activity of a series of 5-(1H-1,2,3-triazolyl) methyl- and 5-acetamidomethyl-oxazolidinone derivatives," Mol. Med. Rep. 2016;13(4):3311-18. PMID: 26936341. (Year: 2016).*
PH-23: National Center for Biotechnology Information. PubChem Database. CID=91569579.
PH-205: National Center for Biotechnology Information. PubChem Database. CID=127042400.
PH-211: National Center for Biotechnology Information. PubChem Database. CID=127042742.
Phillips et al., "Synthesis and biological evaluation of novel 5-(hydroxamic acid) methyl oxazolidinone derivatives," European journal of medicinal chemistry 106 (2015): 120-131.
Bae SK, Yang SH, Lee SJ, Kwon JW, Kim WB, Lee DC, Lee MG (2005). Pharmacokinetic changes of DA-7867, a new oxazolidinone, after intravenous and oral administration to rats with short-term and long-term diabetes mellitus induced by streptozotocin. Eur J Phamn Sci 25: 337-345.
Kombian SB, Phillips OA (2011). In vitro electrophysiological investigations of the acute effects of linezolid and novel oxazolidinones on central nervous system neurons. Neuroscience 180: 53-63, doi:10.1016/j. neuroscience.2011.01.06230306-4522(11)00114-X [pii].
Phillips OA, Sharaf LH (2016). Oxazolidinone antimicrobials: a patent review (2012-2015). Expert Opinion on Therapeutic Patents 2016, 26: 591-605, doi:10.1517/13543776.2016.1168807.
Phillips, O. A., Udo, E. E., Ali, A. A. M., & Al-Hassawi, N. (2003). Synthesis and antibacterial activity of 5-substituted oxazolidinones. Bioorganic & medicinal chemistry, 11(1), 35-41.

* cited by examiner

*Primary Examiner* — Theodore R. Howell
(74) *Attorney, Agent, or Firm* — Nath, Goldberg & Meyer; Richard C. Litman

(57) ABSTRACT

Oxazolidinone hydroxamic acid derivatives of the general formula (I):

Formula I

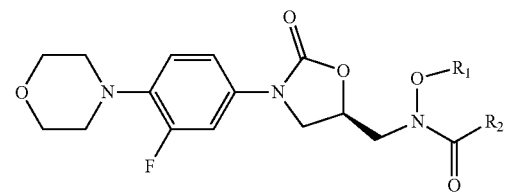

where $R_1$ is hydrogen or hexanoyl and $R_2$ is amino, methyl, ethyl, propyl, isopropyl, cyclopropyl, butyl, isobutyl, cyclobutyl, pentyl, cyclopentyl, hexyl or heptyl, and pharmaceutically acceptable salts thereof, act as dual inhibitors of 5-lipoxygenase and mast cell degranulation. The oxazolidinone hydroxamic acid derivatives or pharmaceutically acceptable salts thereof can be used in the prevention and treatment of asthma and allergies, as well as inflammatory conditions.

10 Claims, 4 Drawing Sheets

OXAZOLIDINONE HYDROXAMIC ACID DERIVATIVES

CROSS-REFERENCE TO RELATED APPLICATION

This application claims the benefit of U.S. Provisional Patent Application Ser. No. 62/969,120, filed Feb. 2, 2020.

BACKGROUND

1. Field

The disclosure of the present patent application relates to oxazolidinone hydroxamic acid derivatives, and particularly to oxazolidinone hydroxamic acid derivatives, compositions containing such compounds, and methods of treating allergic and inflammatory diseases by administering effective amounts of the compounds.

2. Description of the Related Art

Leukotrienes (LTs) are pro-inflammatory mediators generated by the enzyme 5-lipoxygenase (5-LO). There are two classes of LTs: the cysteinyl-LTs (comprising leukotrienes $C_4$ ($LTC_4$), $D_4$ ($LTD_4$) and $E_4$ ($LTE_4$)) and the non-cysteinyl leukotriene $B_4$ ($LTB_4$). LTs are particularly implicated in the pathogenesis and chronicity of allergic diseases such as asthma, allergic rhinitis, allergic conjunctivitis, urticaria and atopic eczema/dermatitis. In addition to the allergic diseases, the LTs are also implicated in many other inflammatory diseases, including cardiovascular diseases (e.g., atherosclerosis and myocardial infarction), arthritis, and certain forms of cancer.

LTs are produced by a number of cell types, especially mast cells, eosinophils, neutrophils, monocytes, and macrophages. Mast cells are prominent pro-inflammatory cells in the pathophysiology of asthma and other allergic or inflammatory diseases. The primary trigger of all allergic diseases is the interaction between an allergen and the specific immunoglobulin E (IgE) molecules bound to the high affinity IgE receptor (FcεRI) on the surface of mast cells of sensitized individuals. This results in the degranulation of the mast cells and the consequent release of pre-formed allergic and inflammatory mediators, such as histamines, proteases (e.g., tryptases), matrix proteinases and stored cytokines (e.g., TNF-α, IL-4, IL-13 and GM-CSF). All of these mediators, and the LTs mentioned above, participate in the pathophysiology and chronicity of allergic and inflammatory related diseases.

In the asthmatic lung, LTs and mast cell produced mediators cause various characteristic symptoms of allergic and inflammatory diseases, such as bronchoconstriction, bronchial inflammation, airway hyper-responsiveness and airway tissue remodeling. Different drugs are conventionally used to address different symptoms, i.e., inhibitors of 5-lipoxygenase (e.g., zileuton) and inhibitors of mast cell degranulation (e.g., cromolyn sodium and nedocromil sodium) are currently used in the prevention or treatment of allergic or inflammatory diseases. Zileuton (±)1-(1-(benzo[b]thiophen-2-yl)ethyl)-1-hydroxyurea, a $Fe^{3+}$-chelating type 5-LO inhibitor, is a "type B hydroxamic acid derivative" and the only 5-LO inhibitor currently approved for clinical use in the treatment of asthma. However, zileuton is plagued with significant drawbacks, such as liver toxicity, weak potency and short half-life, thus requiring higher frequency of administration accompanied by liver enzyme tests.

Further, no known 5-lipoxygenase inhibitor is an effective inhibitor of mast cell degranulation. The IgE-dependent activation of mast cells results in the release of allergic mediators stored in their granules (degranulation)—a process that is unaffected by currently available 5-LO inhibitors. Even steroids, which are the current mainstay of anti-inflammatory therapy, lack an acute and direct effect on degranulation of mast cells, and steroids also have many side effects.

Oxazolidinones are compounds that contain a 5-membered heterocyclic ring, in which a carbonyl group is located between the ring nitrogen and oxygen atoms. Oxazolidinone derivatives, exemplified by the drug linezolid, are best known for their antimicrobial activities.

Thus, oxazolidinone hydroxamic acid derivatives, useful as dual inhibitors of 5-lipoxgygenase and mast cell degranulation for prevention and treatment of asthma, allergies and inflammatory diseases, solving the aforementioned problems is desired.

SUMMARY

The oxazolidinone hydroxamic acid derivatives are of the general formula (I):

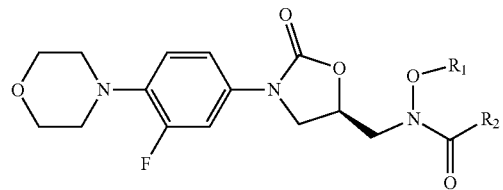

Formula I where $R_1$ is hydrogen or hexanoyl and $R_2$ is amino, methyl, ethyl, propyl, isopropyl, cyclopropyl, butyl, isobutyl, cyclobutyl, pentyl, cyclopentyl, hexyl or heptyl, and pharmaceutically acceptable salts thereof.

The oxazolidinone hydroxamic acid derivatives are potent inhibitors of 5-lipoxygenase as well as inhibitors of mast cell degranulation and useful in treating allergic or inflammatory diseases. Unlike conventional drugs, the oxazolidinone hydroxamic acid derivatives can provide both pharmacological properties, i.e., inhibition of 5-lipoxygenase and inhibition of mast cell degranulation, at clinically relevant concentrations. Thus, the oxazolidinone hydroxamic acid derivatives can prevent and treat asthma and allergies, as well as inflammatory conditions.

A method of treating an allergic or inflammatory disease may include administering to a patient in need thereof an effective amount of at least one of the oxazolidinone hydroxamic acid derivatives.

A pharmaceutical composition may include non-toxic, inert pharmaceutical suitable excipients, and one or more active compounds including at least one of the oxazolidinone hydroxamic acid derivatives.

A method of making the pharmaceutical composition may include mixing at least one of the oxazolidinone hydroxamic acid derivatives under sterile conditions with a pharmaceutically acceptable carrier and preservatives, buffers, or propellants to create the pharmaceutical composition; and providing the pharmaceutical composition in a form suitable for daily, weekly, or monthly administration.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
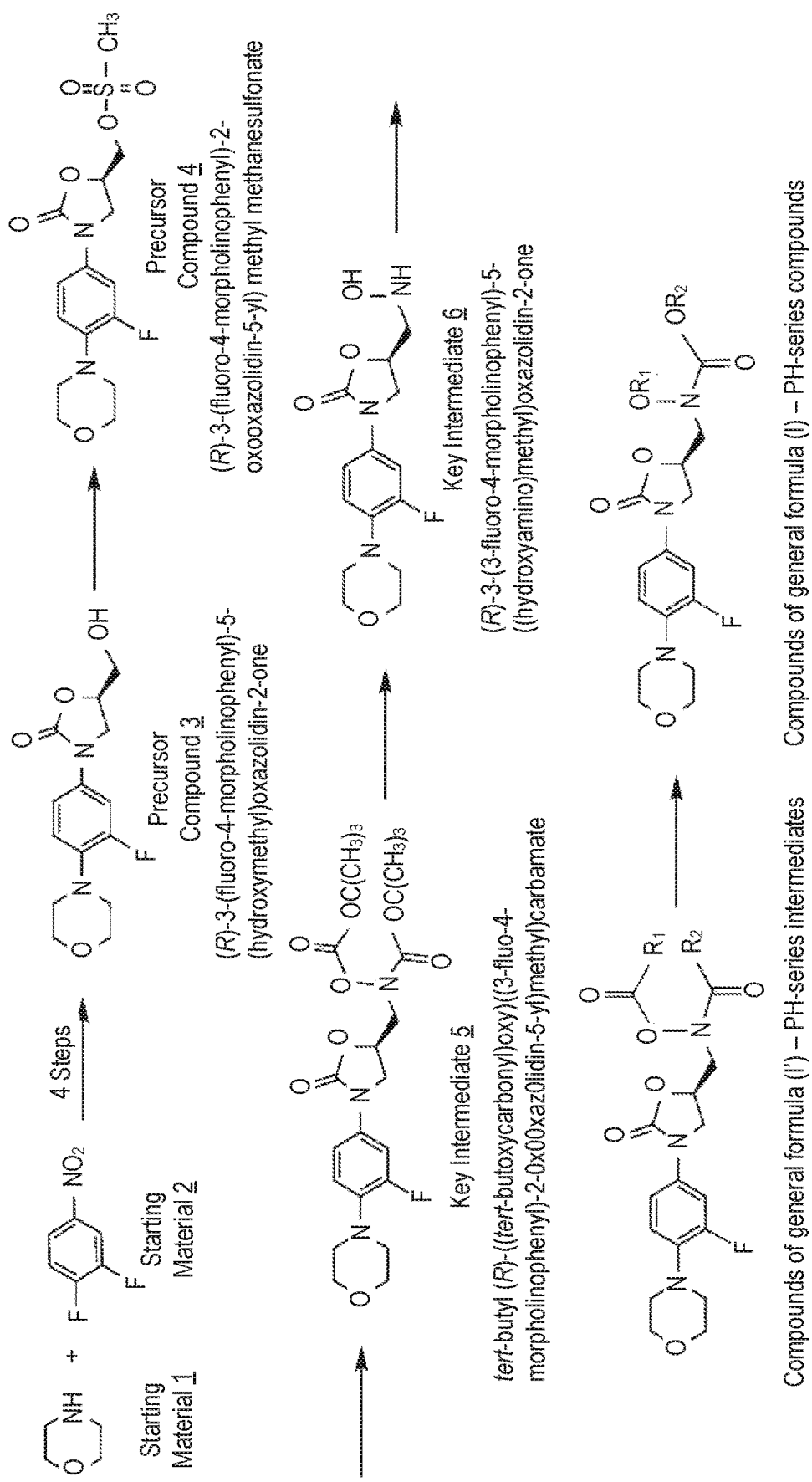
FIG. 1 depicts the reaction scheme for synthesis of the oxazolidinone hydroxamic acid derivatives.

The oxazolidinone hydroxamic acid derivatives are of the general formula (I):

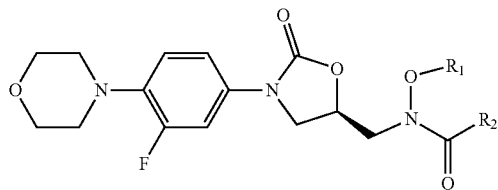

Formula I where $R_1$ is hydrogen or hexanoyl and $R_2$ is amino, methyl, ethyl, propyl, isopropyl, cyclopropyl, butyl, isobutyl, cyclobutyl, pentyl, cyclopentyl, hexyl or heptyl, and pharmaceutically acceptable salts thereof.

The oxazolidinone hydroxamic acid derivatives are potent inhibitors of 5-lipoxygenase as well as inhibitors of mast cell degranulation and useful in treating allergic and/or inflammatory diseases.

A method of treating an allergic and/or inflammatory disease may include administering to a patient in need thereof an effective amount of at least one of the oxazolidinone hydroxamic acid derivatives.

A pharmaceutical composition may include non-toxic, inert pharmaceutical suitable excipients, and one or more active compounds including at least one of the oxazolidinone hydroxamic acid derivatives. The pharmaceutical composition may be in a form suitable for daily, weekly, or monthly administration. The form of the pharmaceutical composition may be a tablet, pill, capsule, granule, powder, ointment, sterile parenteral solution or suspension, metered aerosol or liquid spray, drops, ampule, injection, teaspoonful, or suppository.

A method of making the pharmaceutical composition may include mixing at least one of the oxazolidinone hydroxamic acid derivatives with a pharmaceutically acceptable carrier. For example, the method of making a pharmaceutical composition may include mixing the oxazolidinone hydroxamic acid derivatives under sterile conditions with a pharmaceutically acceptable carrier and preservatives, buffers, or propellants to create the pharmaceutical composition; and providing the pharmaceutical composition in a form suitable for daily, weekly, or monthly administration. The pharmaceutical composition may be administered orally, nasally, rectally, parenterally, intracisternally, intravaginally, intraperitoneally, topically, transdermally, or by surgical implantation. The pharmaceutical composition may be administered in a form selected from liquid oral preparations, solid oral preparations, parenteral preparations, injectable suspensions, and liposomes.

The oxazolidinone hydroxamic acid derivatives or pharmaceutical compositions can be administered to a subject by any suitable route. For example, the compositions can be administered orally (including bucally and sublingually), nasally, rectally, intracisternally, intravaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body, such as in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

A pharmaceutical composition may include one or more of the oxazolidinone hydroxamic acid derivatives. To prepare the pharmaceutical composition, one or more of the oxazolidinone hydroxamic acid derivatives or a salt thereof, as the active ingredient, is intimately admixed with a pharmaceutically acceptable carrier according to conventional pharmaceutical compounding techniques. Carriers may include inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

For parenteral use, the carrier will usually comprise sterile water, though other ingredients, for example, for purposes such as aiding solubility or for preservation, may be included. Injectable suspensions may also be prepared, in which case appropriate liquid carriers, suspending agents, and the like may be employed. Accordingly, the pharmaceutically acceptable carrier can include alcohol, dimethyl sulfoxide (DMSO), a physiological saline, a lipid-based formulation, a liposomal formulation, a nanoparticle formulation, a micellar formulation, a water soluble formulation, a biodegradable polymer, an aqueous preparation, a hydrophobic preparation, a lipid-based vehicle, or a polymer formulation.

The oxazolidinone hydroxamic acid derivatives also can be administered in the form of liposomes. Liposomes generally are derived from phospholipids or other lipid substances and are formed by mono- or multi-lamellar hydrated liquid crystals dispersed in an aqueous medium. Any non-toxic, physiologically acceptable and metabolizable lipid capable of forming liposomes can be used. The present compositions in liposome form can include, in addition to a compound of the present disclosure, stabilizers, preservatives, excipients, and the like. The preferred lipids are the phospholipids and the phosphatidyl cholines (lecithins), both natural and synthetic.

Pharmaceutical compositions for parenteral injection can include pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol, and the like), and suitable mixtures thereof, vegetable oils (such as olive oil), and injectable organic esters, such as ethyl oleate. Proper fluidity can be maintained, for example, by the use of coating materials, such as lecithin, by the maintenance of the required particle size in the case of dispersions, and by the use of surfactants.

The present compositions can include adjuvants, such as preservatives, wetting agents, emulsifying agents, and dispersing agents. Prevention of the action of microorganisms can be ensured by the inclusion of various anti-bacterial and anti-fungal agents, for example, paraben, chlorobutanol, phenol sorbic acid, and the like. It also may be desirable to include isotonic agents, such as sugars, sodium chloride, and the like. Prolonged absorption of the injectable pharmaceutical form can be brought about by the inclusion of agents that delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

A therapeutically effective amount of the oxazolidinone hydroxamic acid derivatives or an amount effective to treat or prevent an allergic or inflammatory disease may be determined initially from the Examples described herein and adjusted for specific oxazolidinone hydroxamic acid derivatives using routine methods.

As will be shown, exemplary oxazolidinone hydroxamic acid derivatives were synthesized and their biological activities as anti-inflammatory, antimicrobial, and antioxidant agents were assessed. An exemplary synthetic scheme for preparation of the oxazolidinone hydroxamic acid derivatives having general formula I is shown in FIG. 1. Starting from commercially available morpholine (starting material 1) and 3,4-diflouronitrobenzene (starting material 2), precursor compound 3 {(R)-3-(3-fluoro-4-morpholinophenyl)-5-(hydroxymethyl)oxazolidin-2-one}, a chiral alcohol, was formed and used to subsequently prepare precursor compound 4 {(R)-(3-(3-fluoro-4-morpholinophenyl)-2-oxooxazolidin-5-yl)methyl methanesulfonate} according to Brickner et al., 1996 (Brickner, S. J., et al. *Journal of medicinal chemistry*, 39(3), 673-679(1996)); Phillips et al., 2003 (Phillips, O. A., et al., *Bioorganic & medicinal chemistry*, 11(1), 35-41. (2003)); and Phillips et al. 2015 (Phillips, O. A., et al. *European journal of medicinal chemistry*, 106, 120-131 (2015)). Intermediate compound 5 {tert-butyl (R)-((tert-butoxycarbonyl)oxy)((3-(3-fluoro-4-morpholinophenyl)-2-oxooxazolidin-5-yl)methyl)carbamate} was synthesized by treating precursor compound 4 with a sodium salt of tert-butyl N-(tert-butoxycarbonyloxy)carbamate in anhydrous dimethylformamide (DMF) according to Phillips, et al., 2003 (Phillips, O. A., et al., *Bioorganic & medicinal chemistry*, 11(1), 35-41. (2003)); and Phillips et al. 2015 (Phillips, O. A., et al. *European journal of medicinal chemistry*, 106, 120-131 (2015)). Deprotection of the tert-boc groups of intermediate compound 5 by trifluoroacetic acid in DCM, followed by treatment with an aqueous solution of potassium carbonate produces intermediate N-hydroxylamine compound 6 {(R)-3-(3-fluoro-4-morpholinophenyl)-5-((hydroxyamino)methyl)oxazolidin-2-one. Further acylation of the —NHOH functional group of intermediate compound 6 affords N-alkanoxy-N-((3-3-fluoro-4-morpholinophenyl)-2-oxooxazolidin-5-yl) methyl) alkanamide derivatives, compounds of general formula (I')—referred to herein as PH-series intermediates. Furthermore, selective deprotection of the N-acetate group of the PH-series intermediates under basic reaction conditions gives the respective morpholinyl-N-hydroxamic acid containing oxazolidinone derivative compounds of general formula (I), referred to alternatively as PH-series compounds. The PH-series intermediates and compounds referred to herein are defined according to the variable moieties $R_1$ and $R_2$ defined in Table 1.

The following examples illustrate the present teachings.

Example 1

General Synthesis Procedures

Preparation of Key Intermediate 6: (R)-3-(3-fluoro-4-morpholinophenyl)-5-((hydroxyamino)methyl)oxazolidin-2-one

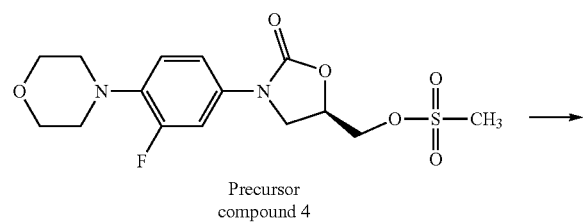

Precursor compound 4

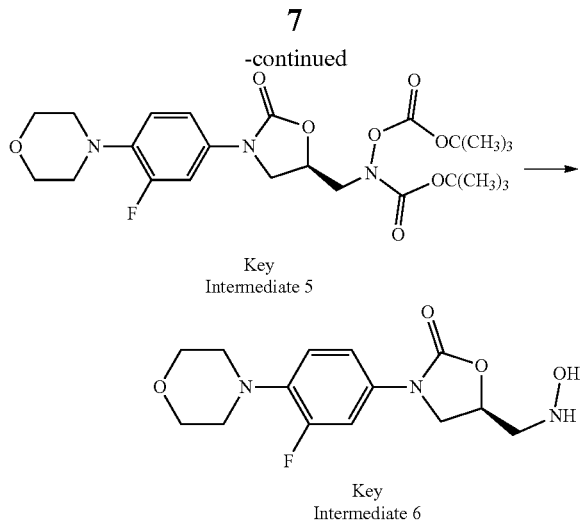

Key Intermediate 5

Key Intermediate 6

An ice cooled (0° C.) solution of tert-butyl N-(tert-butoxycarbonyloxy) carbamate (4.97 g, 21.31 mmol) in anhydrous DMF (30 mL) under nitrogen was treated portion-wise with 60% sodium hydride in mineral oil (770 mg, 22.75 mmol) and stirred for 30 minutes. The reaction mixture was treated with drop-wise addition of a solution of [N-3-(3-fluoro-4-morpholinylphenyl)-2-oxo-5-oxazolidinyl] methyl methanesulfonate (precursor compound 4: 6.00 g, 16.02 mmol) in DMF (70 mL). The reaction mixture was stirred at room temperature for 60 hours. The reaction was quenched by addition of water. Reaction product was extracted with ethyl acetate, washed with water, washed with brine, dried (Na$_2$SO$_4$), filtered and concentrated to give a crude product as a brownish oil. Silica gel column chromatography eluted with EtOAc-Hexane 2:1 gave key intermediate compound 5 as a pale-yellow viscous oil (7.0 g, yield, 85%) that solidifies upon cooling in the fridge to a yellow solid. $^1$H-NMR (DMSO-d$_6$, 600 MHz): δ 7.51 (dd, 1H, J=15.0 Hz, 2.5 Hz, phenyl H), 7.19 (dd, 1H, J=8.8 Hz, 2.5 Hz, phenyl H), 7.09 (t, 1H J=9.6 Hz, phenyl H), 4.87 (m, 1H, oxazolidinone H), 4.15 (t, 1H, J=4.6 Hz, oxazolidinone H), 3.97 (m, 1H, oxazolidinone H), 3.82 (m, 1H, methylene H), 3.72-3.76 (br t, 5H, morpholine H and methylene H), 2.97 (br t, 4H, morpholine H), 1.41-1.48 (br, 18H). LRMS 511.2 (M$^+$).

The key intermediate compound 5 (14.69 g, 28.71 mmol) was dissolved in anhydrous DCM (25 mL) and cooled to 0° C. in an ice-bath. This solution was treated with rapid drop wise addition of trifluoroacetic acid (20 mL) and the reaction mixture was stirred overnight. The reaction mixture was concentrated to dryness to give a gummy residue, which was treated with a 10% potassium carbonate solution in water to give a basic solution. The resulting gelatinous precipitate was collected by filtration to give key intermediate compound 6 as an off-white solid (8.64 g, yield, 94%), mp 134-137° C. This product was used for further reactions without purification. $^1$H-NMR (DMSO-d$_6$, 400 MHz): δ 7.50 (dd, 1H, J=15.1 Hz, 2.5 Hz, phenyl H), 7.45 (s, N—OH, 1H), 7.20 (dd, 1H, J=2.1 Hz, 8.7 Hz, phenyl H), 7.06 (t, 1H, J=9.6 Hz, phenyl H), 6.02 (br, s, 1H, N—H), 4.70-4.83 (m, 1H, oxazolidinone H), 4.09 (t, 1H, J=8.9 Hz, oxazolidinone H), 3.82 (dd, 1H, J=6.8 Hz, 8.9 Hz, oxazolidinone H), 3.73 (br. t, 4H, J=4.6 Hz, morpholine H), 2.97-3.10 (br. m, 2H, CH$_2$N(OH)H, partially overlaps with the morpholine triplet signal), 2.96 (t, 4H, J=4.6 Hz, morpholine H, partially overlaps with the CH$_2$N(OH)H signal). $^{13}$C-NMR (DMSO-d$_6$, 600 MHz): δ 165.28, 155.35, 154.21, 153.74, 135.42, 135.37, 133.64, 133.57, 119.19, 119.17, 114.04, 114.02, 106.69, 106.52, 70.66, 70.04, 66.11, 56.31, 50.68, 48.12. MS 311.2 (M$^+$).

General procedure for the synthesis of (R)—N-((3-(3-fluoro-4-morpholinophenyl)-2-oxooxazolidin-5-yl)methyl)-N-hydroxyalkanamide derivatives (PH-series compounds): A solution of intermediate compound 6 (1.0 eq.) in anhydrous DCM or CH$_3$CN (30-50 mL) was treated with triethylamine (6.0 eq.) and dropwise addition of the respective acid anhydride or acid chloride (3.0 eq.) at 0° C., and stirred to room temperature overnight. The reaction mixture was diluted with a 10% solution of potassium carbonate (20 mL) and the DCM layer was separated and washed with water, washed with brine, dried (Na$_2$SO$_4$), filtered and concentrated to give the crude product. Purification by normal phase silica gel column chromatography and/or recrystallized using suitable organic solvent mixtures to give the compounds of general formula (I')—PH-series intermediates—{N-alkanoxy-N-((3-3-fluoro-4-morpholinophenyl)-2-oxooxazolidin-5-yl) methyl) alkanamide} derivatives. A solution of the compounds of general formula (I')—PH-series intermediates (1 eq) in methanol:tetrahydrofuran (THF) (4:1, v/v) was stirred at 0° C. and treated with a 1.0 eq. NaOH solution in water (~20 mL). The reaction mixture was stirred for 1 hr and 10 min and neutralized to a pH of ~7 by addition of a solution of 1.0 eq. HCl in water (30 mL). The reaction mixture was concentrated to remove THF and methanol and the aqueous residue was saturated with NaCl and extracted with DCM. The organic layer was separated, washed with brine, dried (Na$_2$SO$_4$), filtered and concentrated to give the crude product. Purification was performed either by silica gel column chromatography and/or recrystallization using suitable organic solvents to give the compounds of general formula (I)—PH-series compounds—{ (R)—N-((3-(3-fluoro-4-morpholinophenyl)-2-oxooxazolidin-5-yl)methyl)-N-hydroxy-alkanamide} derivatives as the final products.

Example 2

Synthesis of Specific Oxazolidinone Hydroxamic Acid Derivatives

The following specific examples are intended to be illustrative of the present subject matter and not limiting.

Compound PH-238: (R)-1-((3-(3-fluoro-4-morpholinophenyl)-2-oxooxazolidin-5-yl)methyl)-1-hydroxyurea

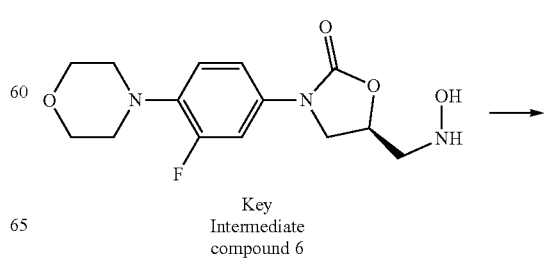

Key Intermediate compound 6

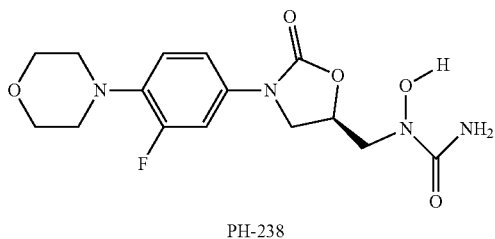

PH-238

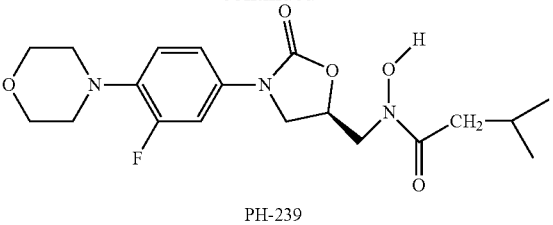

PH-239

A mixture of intermediate compound 6 (1.46 g, 5.272 mmol) in THF (5 mL) and dioxane (15 mL) was treated with trimethylsilyl-isocyanate (0.862 mL, 6.315 mmol) and heated at 80° C. for 1 hr. The reaction mixture was cooled and poured onto an ice cold saturated $NH_4Cl$ solution and extracted with EtOAc (50 mL). The EtOAc extract was washed with brine, dried $Na_2SO_4$, filtered and concentrated and the residue triturated with $Et_2O$ to give an off-white solid after filtration. Purification by recrystallization from EtOAc gave PH-238, as an off-white solid. 700 mg, 38% yield, mp 125-128° C. $^1$H-NMR (DMSOd$_6$, 600 MHz): δ 9.59 (s, 1H, NOH, exchangeable with $D_2O$), 7.50 (dd, 1H, J=2.4 Hz, 15.0 Hz, phenyl H), 7.18 (dd, 1H, J=2.0 Hz, 8.6 Hz, phenyl H), 7.06 (t, 1H, J=9.3 Hz, phenyl H), 6.76 (s, 2H, $NH_2$, exchangeable with $D_2O$), 4.80-4.85 (m, 1H, oxazolidinone H), 4.11 (t, 1H, J=8.9 Hz, oxazolidinone H), 3.76-3.84 (m, 2H, oxazolidinone H and methylene H), 3.73 (t, 4H, J=4.4 Hz, morpholine H), 3.53 (dd, 1H, J=5.1 Hz, 14.5 Hz methylene H), 2.96 (t, 4H, J=4.3 Hz, morpholine H). $^{13}$C-NMR (DMSO-d$_6$, 600 MHz): δ 161.48, 155.38, 153.94, 153.76, 135.52, 133.56, 119.24, 114.10, 106.75, 106.57, 70.45, 66.14, 52.64, 50.70, 47.63. IR (KBr pellet, cm$^1$): ν 3448, 3380, 2960, 2898, 2858, 1749, 1658, 1576, 1518, 1484, 1448, 1419, 1326, 1231, 1114. HRMS (m/z): Calcd for $C_{15}H_{19}FN_3O_5$: 354.1339, found 355.1417 (M$^+$+H), LRMS (m/z): 354.1334 (M$^+$).

Compound PH-239: (R)—N-((3-(3-fluoro-4-morpholinophenyl)-2-oxooxazolidin-5-yl)methyl)-N-hydroxy-3-methylbutanamide

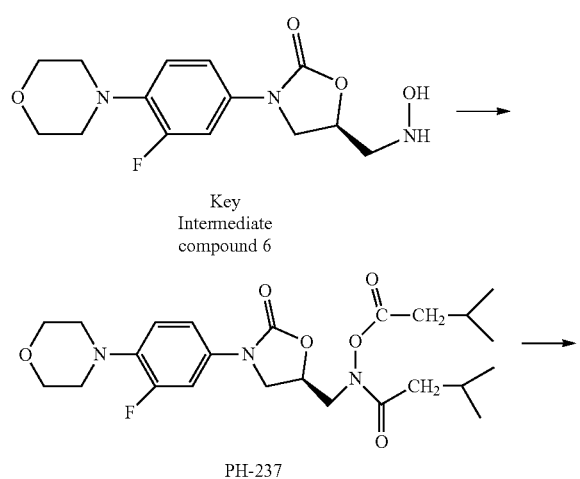

Key Intermediate compound 6

PH-237

Compound PH-237 was prepared from intermediate compound 6 (1.50 g, 4.82 mmol), isovaleric anhydride (2.83 mL, 14.46 mmol), triethylamine (4.05 mL; 28.41 mmol) in anhydrous DCM (30 mL) to give a crude product. Purification by silica gel column chromatography (EtOAc-Hexane, 1:2 to 1:1) gave intermediate (R)—N-((3-(3-fluoro-4-morpholinophenyl)-2-oxooxazolidin-5-yl)methyl)-3-methyl-N-((3-methylbutanoyl)oxy)butanamide (PH-237) as a white solid. 0.815 g yield, 35%, m.p. 89-90° C. $^1$H-NMR (CDCl$_3$, 600 MHz): δ 7.46 (dd, 1H, J=2.6 Hz, 14.3 Hz, phenyl H), 7.11 (m, 1H, phenyl H), 6.94 (t, 1H, J=9.1 Hz, phenyl H), 4.80-4.84 (br. m, 1H, oxazolidinone H), 4.10 (d, 2H, J=4.6 Hz, methylene $CH_2$), 4.05 (t, 1H, J=8.9 Hz, oxazolidinone H), 3.88-3.91 (m, 5H, morpholine H and oxazolidinone H), 3.07 (t, 4H, J=4.7 Hz, morpholine H), 2.39 (d, 2H, J=7.1 Hz, $NOCOCH_2CH(CH_3)_2$), 2.19-2.51 (m, 1H, $NOCOCH_2CH(CH_3)_2$), 2.06-2.12 (m, 3H, $NCOCH_2CH(CH_3)_2$ and $NOCOCH_2CH(CH_3)_2$), 1.05 (dd, 6H, J=1.4 Hz, 6.6 Hz, $NOCOCH_2CH(CH_3)_2$), 0.93 (dd, 6H, J=6.1 Hz, 13.0 Hz, $NCOCH_2CH(CH_3)_2$). $^{13}$C-NMR (DMSO-d$_6$, 600 MHz): δ 155.33, 153.70, 135.58, 135.52, 133.35, 133.28, 119.23, 119.20, 114.13, 114.12, 106.75, 106.58, 70.12, 66.10, 50.66, 50.65, 47.15, 24.95, 22.14, 22.11, 22.01. IR (KBr pellet, cm$^{-1}$): ν 2960, 2871, 2822, 1797, 1759, 1672, 1520, 1471, 1445, 1404, 1329, 1289, 1169, 1136, 1119, 1065. MS 479.4 (M$^+$). Anal calcd for $C_{24}H_{34}FN_3O_6$: C: 60.11, H: 7.15, N: 8.76; found C: 59.71, H: 7.41, N: 8.55.

A solution of compound PH-237 (0.80 g, 1.67 mmol) in MeOH:THF (28 ml:7 ml) was treated with NaOH solution (133 mg in 20 mL water). Purification by recrystallization (EtOAc-hexane 2:1) gave the compound PH-239 as a white solid. (328 mg, yield, 55%, m.p. 122-124.5° C. $^1$H-NMR (DMSO-d$_6$, 600 MHz): δ 9.93 (s, 1H, N—OH, exchangeable with $D_2O$), 7.48 (dd, 1H, J=2.5 Hz, 14.9 Hz, phenyl H), 7.17 (dd, 1H, J=2.3 Hz, 8.7 Hz, phenyl H), 7.06 (t, 1H, J=8.4 Hz, phenyl H), 4.85-4.90 (br. m, 1H, oxazolidinone H), 4.13 (t, 1H, J=8.9 Hz, oxazolidinone H), 4.05 (dd, 1H, J=6.5 Hz, 13.7 Hz, oxazolidinone H), 3.72-3.76 (m, 5H, morpholine H and methylene H), 3.67 (dd, 1H, J=4.5 Hz, 14.6 Hz, methylene H), 2.96 (t, 4H, J=4.6 Hz, morpholine H), 2.25-2.30 (m, 2H, $NCOCH_2CH(CH_3)_2$), 1.99-2.04 (m, 1H, $NCOCH_2CH(CH_3)_2$), 0.88 (t, 6H, J=5.9 Hz, $NCOCH_2CH(CH_3)_2$). $^{13}$C-NMR (DMSO-d$_6$, 600 MHz): δ 173.22, 155.36, 153.95, 153.74, 135.56, 135.50, 133.47, 133.39, 119.25, 119.22, 114.12, 114.10, 106.75, 106.57, 69.87, 66.13, 50.69, 50.68, 50.27, 47.48, 24.42, 22.47, 22.49. IR (KBr pellet, cm$^{-1}$): ν 3384, 3196, 2955, 2869, 1752, 1729, 1633, 1610, 1521, 1447, 1429, 1333, 1272, 1233, 1173, 1119, 1068. HRMS (m/z): Calcd for $C_{19}H_{26}FN_3O_5$: 395.1856, found 396.1874 (M$^+$+H), LRMS (m/z): 395.2 (M$^+$). Anal calcd for $C_{19}H_{26}FN_3O_5$: C: 57.71, H: 6.63, N: 10.63; found C: 57.28, H: 6.94, N: 10.32.

Compound PH-241: (R)—N-((3-(3-fluoro-4-morpholinophenyl)-2-oxooxazolidin-5-yl)methyl)-N-hydroxypentanamide

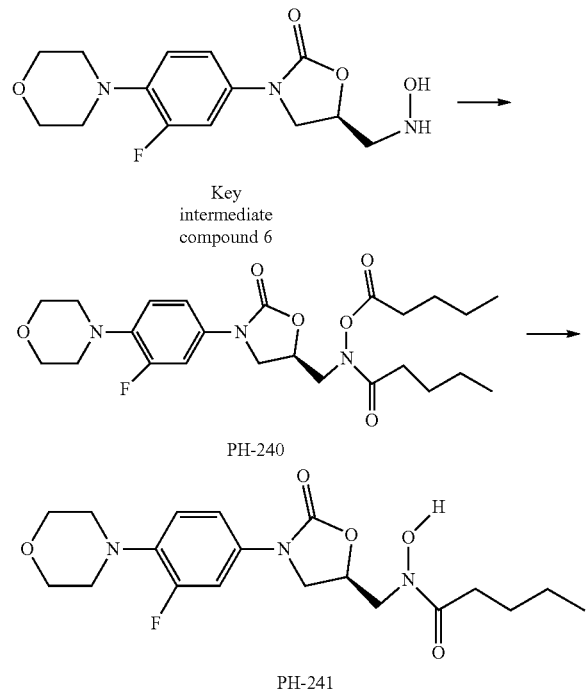

Compound PH-240 was prepared from the intermediate compound 6 (2.20 g, 7.07 mmol), valeric anhydride (4.18 mL, 21.20 mmol), triethylamine (5.94 mL; 42.40 mmol) in anhydrous DCM (30 mL) to give a crude product. Purification by silica gel column chromatography (EtOAc-Hexane, 1:2 to 1:1) gave PH-240, (R)—N-((3-(3-fluoro-4-morpholinophenyl)-2-oxooxazolidin-5-yl)methyl)-N-(pentanoyloxy)pentamide, as a white solid 1.10 g, yield, 33%, m.p. 75-77.5° C. $^1$H-NMR (DMSO-d$_6$, 600 MHz): δ 7.48 (dd, 1H, J=2.5 Hz, 14.9 Hz, phenyl H), 7.18 (dd, 1H, J=2.2 Hz, 8.8 Hz, phenyl H), 7.07 (t, 1H, J=9.4 Hz, phenyl H), 4.84-4.88 (br. m, 1H, oxazolidinone H), 4.10-4.19 (br., 1H, oxazolidinone H, overlapping with oxazolidinone H triplet), 4.11 (t, 1H, J=9.0 Hz, oxazolidinone H, overlapping with the broad oxazolidinone H signal), 3.84-3.92 (br., 1H, methylene H), 3.74 (t, 5H, J=4.6 Hz, morpholine H and methylene H), 2.96 (t, 4H, J=4.6 Hz, morpholine H), 2.50 (br., 2H, methylene —CH$_2$— overlapping with DMSO signal), 2.11-2.27 (br., 2H, methylene H), 1.56-1.61 (m, 2H, methylene H), 1.40-1.50 (br., 2H, methylene —CH$_2$—), 1.31-1.37 (m, 2H, methylene H) 1.20-1.29 (br. 2H, methylene H), 0.88 (t, 3H, J=7.4 Hz, methyl H), 0.82 (br. t, 6H, J=6.5 Hz, methyl H). $^{13}$C-NMR (DMSO-d$_6$, 600 MHz): δ 155.36, 153.75, 135.59, 135.53, 133.37, 133.30, 119.25, 119.22, 114.14, 114.12, 106.75, 106.57, 70.16, 66.13, 50.69, 50.67, 47.15, 30.85, 30.75, 25.97, 21.55, 21.49, 13.62, 13.49. IR (KBr pellet, cm$^1$): v 2963, 2930, 2857, 1797, 1739, 1683, 1627, 1572, 1518, 1447, 1409, 1327, 1236, 1214, 1138, 1120, 1057. HRMS (m/z): Calcd for C$_{24}$H$_{34}$FN$_3$O$_6$: 479.2432, found 480.2300 (M$^+$+H), LRMS (m/z): 479.3 (M$^+$). Anal calcd for C$_{24}$H$_{34}$FN$_3$O$_6$: C: 60.11; H: 7.15; N: 8.76; found C: 60.06; H, 6.87; N, 8.74.

A solution of compound PH-240 (0.900 g, 1.88 mmol) in MeOH:THF (28 ml:7 ml) was treated with NaOH solution (150 mg in 20 mL water). Purification by recrystallization (EtOAc-hexane 2:1) gave compound PH-241 as an off-white solid. 700 mg, yield, 94%, m.p. 121° C.-122.5° C. $^1$H-NMR (DMSO-d$_6$, 600 MHz): δ 9.94 (s, 1H, N—OH, exchangeable with D$_2$O), 7.48 (dd, 1H, J=2.5 Hz, 15.0 Hz, phenyl H), 7.17 (dd, 1H, J=2.3 Hz, 8.9 Hz, phenyl H), 7.06 (t, 1H, J=9.4 Hz, phenyl H), 4.85-4.89 (br. m, 1H, oxazolidinone H), 4.12 (t, 1H, J=8.9 Hz, oxazolidinone H), 4.04 (dd, 1H, J=6.6 Hz, 15.6 Hz, oxazolidinone H), 3.72-3.76 (m, 5H, morpholine H and methylene H), 3.67 (dd, 1H, J=4.6 Hz, 14.9 Hz, methylene H), 2.96 (t, 4H, J=4.7 Hz, morpholine H), 2.36-2.39 (m, 2H, NCOCH$_2$CH$_2$CH$_2$CH$_3$), 1.44-1.48 (m, 2H, NCOCH$_2$CH$_2$CH$_2$CH$_3$), 1.24-1.30 (m, 2H, NCOCH$_2$CH$_2$CH$_2$CH$_3$), 0.85 (t, 2H, J=7.4 Hz, NCOCH$_2$CH$_2$CH$_2$CH$_3$). $^{13}$C-NMR (DMSO-d$_6$, 600 MHz): δ 173.93, 155.33, 153.90, 153.72, 135.51, 135.46, 133.43, 133.36, 119.20, 119.17, 114.10, 114.08, 106.73, 106.55, 69.87, 66.09, 50.66, 50.64, 50.30, 47.45, 31.22, 26.21, 21.81, 13.68. IR (KBr pellet, cm$^{-1}$): v 3187, 2959, 2931, 2860, 1743, 1720, 1626, 1522, 1447, 1425, 1331, 1271, 1234, 1196, 1115, 1071. HRMS (m/z): Calcd for C$_{19}$H$_{26}$FN$_3$O$_5$: 395.1856, found 396.2037 (M$^+$+H), LRMS (m/z): 395.2 (M$^+$). Anal calcd for C$_{19}$H$_{26}$FN$_3$O$_5$: C: 57.71, H: 6.63, N: 10.63; found C: 58.18, H: 6.61, N: 10.39.

Compound PH-245: (R)—N-((3-(3-fluoro-4-morpholinophenyl)-2-oxooxazolidin-5-yl)methyl)-N-hydroxycyclobutane-carboxamide

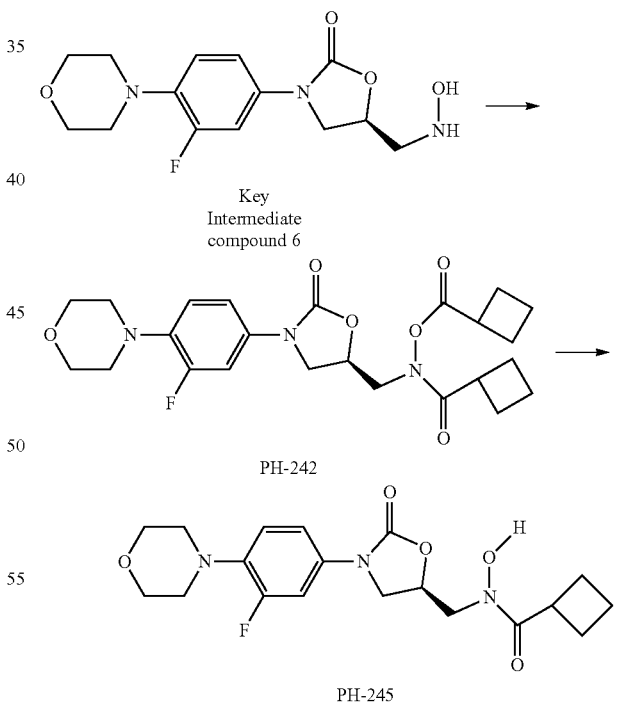

Compound PH-242 was prepared from the intermediate compound 6 (2.20 g, 7.07 mmol), cyclobutanecarbonylchloride (2.42 mL, 21.20 mmol), triethylamine (5.94 mL; 42.40 mmol) in anhydrous DCM (30 mL) to give a brown-yellowish gummy crude product. Purification by silica gel column chromatography (EtOAc-Hexane, 1:2 to 1:1) gave the intermediate (R)—N-((cyclobutanecarbonyl)oxy)-N-((3-(3-fluoro-4-morpholinophenyl)-2-oxooxazolidin-5-yl)methyl)cyclobutanecarboxamide PH-242 as a white solid 0.487 g, yield 15%, m.p. 122-124° C. $^1$H-NMR (DMSO-d$_6$, 600 MHz): δ 7.48 (dd, 1H, J=2.4 Hz, 14.9 Hz, phenyl H), 7.17 (dd, 1H, J=2.3 Hz, 8.8 Hz, phenyl H), 7.07 (t, 1H, J=9.3 Hz, phenyl H), 4.83-4.87 (br. m, 1H, oxazolidinone H), 4.09-4.15 (br., 1H, oxazolidinone H, overlapping with oxazolidinone H triplet), 4.10 (t, 1H, J=9.0 Hz, oxazolidinone H, overlapping with the broad oxazolidinone H signal), 3.87-3.90 (br., 1H, methylene H), 3.73-3.75 (m, 5H, morpholine H and methylene H), 3.32-3.35 (br., 1H, cyclobutane H), 3.09-3.19 (br., 1H, cyclobutane H), 2.96 (t, 4H, J=4.7 Hz, morpholine H), 1.17-2.34 (m, 12H, cyclobutane H). $^{13}$C-NMR (DMSO-d$_6$, 600 MHz): δ 155.35, 153.75, 153.73, 135.59, 135.54, 133.38, 133.30, 119.24, 119.22, 114.16, 106.78, 106.60, 66.12, 50.68, 50.67, 47.15, 34.94, 24.43, 24.32, 24.21, 24.11, 17.99, 17.44. IR (KBr pellet, cm$^{-1}$): ν 2963, 2857, 1788, 1741, 1678, 1517, 1445, 1410, 1329, 1261, 1096, 1021. HRMS (m/z): Calcd for C$_{24}$H$_{30}$FN$_3$O$_6$: 475.2119, found 476.2341 (M$^+$+H), LRMS (m/z): 475.2 (M$^+$). Anal calcd for C$_{24}$H$_{34}$FN$_3$O$_6$: C: 60.62; H: 6.36; N: 8.84; found C: 60.02; H: 6.37; N: 8.84.

A solution of the intermediate compound PH-242 (0.487 g, 1.02 mmol) in MeOH:THF (28 ml:7 ml) was treated with NaOH solution (84 mg in 20 mL water). Purification by recrystallization (EtOAc-hexane 2:1) gave compound PH-245 as off-white solid 248 mg, yield 92%, m.p. 132-133.5° C. $^1$H-NMR (DMSO-d$_6$, 600 MHz): δ 9.80 (s, 1H, N—OH, exchangeable with D$_2$O), 7.49 (dd, 1H, J=2.5 Hz, 14.9 Hz, phenyl H), 7.18 (dd, 1H, J=2.3 Hz, 8.9 Hz, phenyl H), 7.06 (t, 1H, J=9.4 Hz, phenyl H), 4.84-4.89 (br. m, 1H, oxazolidinone H), 4.12 (t, 1H, J=8.9 Hz, oxazolidinone H), 4.02 (dd, 1H, J=6.8 Hz, 14.6 Hz, oxazolidinone H), 3.73-3.76 (m, 5H, morpholine H and methylene H), 3.66 (dd, 1H, J=4.5 Hz, 14.6 Hz, methylene H), 3.46-3.52 (m, 1H, cyclobutane H), 2.96 (t, 4H, J=4.7 Hz, morpholine H), 1.75-1.93 (m, 6H, cyclobutane H). $^{13}$C-NMR (DMSO-d$_6$, 600 MHz): δ 175.29, 155.36, 153.95, 153.74, 135.55, 135.49, 133.45, 133.38, 119.24, 119.21, 114.13, 114.11, 106.75, 106.57, 69.80, 66.13, 50.69, 50.67, 50.56, 47.50, 35.72, 24.39, 17.73. IR (KBr pellet, cm$^1$): ν 3224, 2953, 2858, 1740, 1722, 1629, 1523, 1476, 1425, 1331, 1233, 1198, 1114, 1081. HRMS (m/z): Calcd for C$_{19}$H$_{24}$FN$_3$O$_5$: 393.1700, found 394.1899 (M$^+$+H), LRMS (m/z): 393.2 (M$^+$). Anal calcd for C$_{19}$H$_{24}$FN$_3$O$_5$: C: 58.01, H: 6.15, N: 10.68; found C: 57.61, H: 6.02, N: 10.42.

(R)—N-((3-(3-fluoro-4-morpholinophenyl)-2-oxooxazolidin-5-yl)methyl)-N-hydroxycyclopentane-carboxamide (Compound PH-244

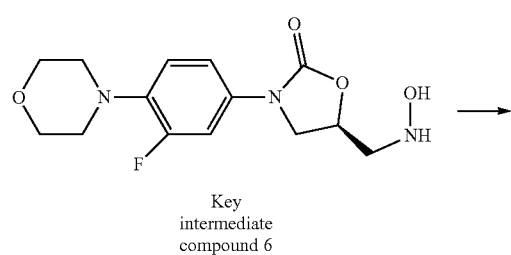

Key intermediate compound 6

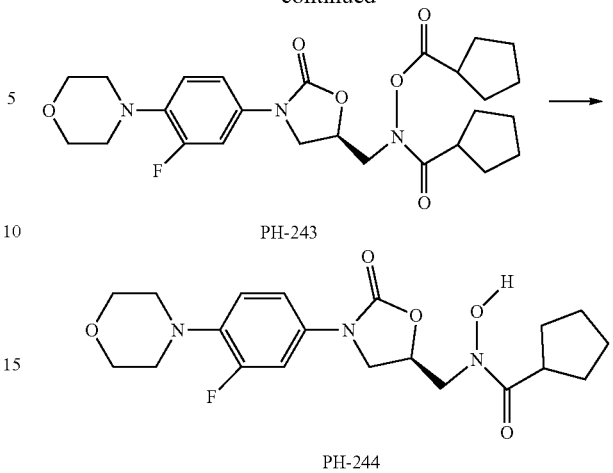

PH-243

PH-244

The intermediate compound PH-243 was prepared from key intermediate compound 6 (2.20 g, 7.07 mmol), cyclopentanecarbonylchloride (2.58 mL, 21.20 mmol), triethylamine (5.94 mL; 42.40 mmol) in anhydrous DCM (30 mL) to give a brown-yellowish gummy crude product. Purification by silica gel column chromatography (EtOAc-Hexane, 1:2 to 1:1) gave PH-243, (R)—N-((cyclopentanecarbonyl)oxy)-N-((3-(3-fluoro-4-morpholinophenyl)-2-oxooxazolidin-5-yl)methyl)cyclopentanecarboxamide as a white solid 1.20 g, yield 34%, recrystallized from EtOAc-Et$_2$O, m.p. 114.5-116° C. $^1$H-NMR (DMSO-d$_6$, 600 MHz): δ 7.48 (dd, 1H, J=2.3 Hz, 14.9 Hz, phenyl H), 7.17 (dd, 1H, J=2.3 Hz, 8.9 Hz, phenyl H), 7.07 (t, 1H, J=9.4 Hz, phenyl H), 4.83-4.88 (br. m, 1H, oxazolidinone H), 4.09-4.16 (br., 1H, oxazolidinone H, overlapping with oxazolidinone H triplet), 4.12 (t, 1H, J=9.0 Hz, oxazolidinone H, overlapping with the broad oxazolidinone H signal), 3.84-3.95 (br., 1H, methylene H), 3.74 (t, 5H, J=4.6 Hz, morpholine H and methylene H), 2.96 (t, 5H, J=4.6 Hz, morpholine H and cyclopentane H), 2.64-2.79 (br., 1H, cyclopentane H), 1.44-1.96 (m, 16H, cyclopentane H). $^{13}$C-NMR (DMSO-d$_6$, 600 MHz): δ 155.33, 153.71, 135.55, 135.50, 133.36, 133.29, 119.23, 119.20, 114.11, 114.09, 106.73, 106.55, 70.24, 66.10, 50.66, 50.65, 47.15, 29.49, 29.22, 29.08, 29.05, 25.53, 25.26. IR (KBr pellet, cm$^{-1}$): ν 2960, 2853, 1779, 1754, 1671, 1515, 1449, 1415, 1327, 1225, 1193, 1117, 1087. HRMS (m/z): Calcd for C$_{26}$H$_{34}$FN$_3$O$_6$: 503.2432, found 504.2700 (M$^+$+H), LRMS (m/z): 503.2 (M$^+$). Anal calcd for C$_{26}$H$_{34}$FN$_3$O$_6$: C: 62.01; H: 6.81; N: 8.34; found C: 62.25; H: 6.64; N: 8.08.

A solution of PH-243 (0.900 g, 1.79 mmol) in MeOH:THF (28 ml:7 ml) was treated with NaOH solution (143 mg in 20 mL water). Purification by recrystallization (EtOAc-hexane 2:1) gave the compound PH-244 as off-white solid 578 mg, yield 76%, recrystallized from EtOAc-Et$_2$O; m.p. 164.5-166.5° C. $^1$H-NMR (DMSO-d$_6$, 600 MHz): δ 9.90 (s, 1H, N—OH, exchangeable with D$_2$O), 7.49 (dd, 1H, J=2.5 Hz, 15.00 Hz, phenyl H), 7.18 (dd, 1H, J=2.3 Hz, 8.8 Hz, phenyl H), 7.06 (t, 1H, J=9.4 Hz, phenyl H), 4.84-4.89 (br. m, 1H, oxazolidinone H), 4.13 (t, 1H, J=8.9 Hz, oxazolidinone H), 4.02 (dd, 1H, J=6.5 Hz, 14.2 Hz, oxazolidinone H), 3.73-3.76 (m, 5H, morpholine H and methylene H), 3.68 (dd, 1H, J=4.2 Hz, 14.6 Hz, methylene H), 3.10-3.20 (m, 1H, cyclopentane H), 2.96 (t, 4H, J=4.6 Hz, morpholine H), 1.45-1.80 (m, 8H, cyclopentane H). $^{13}$C-NMR (DMSO-d$_6$, 600 MHz): δ 176.77, 155.36, 153.96, 153.74, 135.54, 135.48, 133.47, 133.39, 119.24, 119.21, 114.10, 114.08, 106.73, 106.55, 69.90, 66.99, 66.13, 50.69, 50.68, 50.58, 47.48, 30.66, 29.27, 29.20, 25.58, 25.56 IR (KBr pellet, cm$^1$): v 3301, 2964, 2869, 1752, 1655, 1640, 1520, 1477, 1444, 1398, 1328, 1239, 1132, 1107. HRMS (m/z): Calcd for $C_{20}H_{26}FN_3O_5$: 407.1856, found 408.2039 (M$^+$+H), LRMS (m/z): 407.2 (M$^+$). Anal calcd for $C_{20}H_{26}FN_3O_5$: C, 58.96; H, 6.43; N, 10.31; found C, 58.57; H, 6.31; N, 10.01.

Compound PH-247: (R)—N-((3-(3-fluoro-4-morpholinophenyl)-2-oxooxazolidin-5-yl) methyl)-N-hydroxyhexanamide

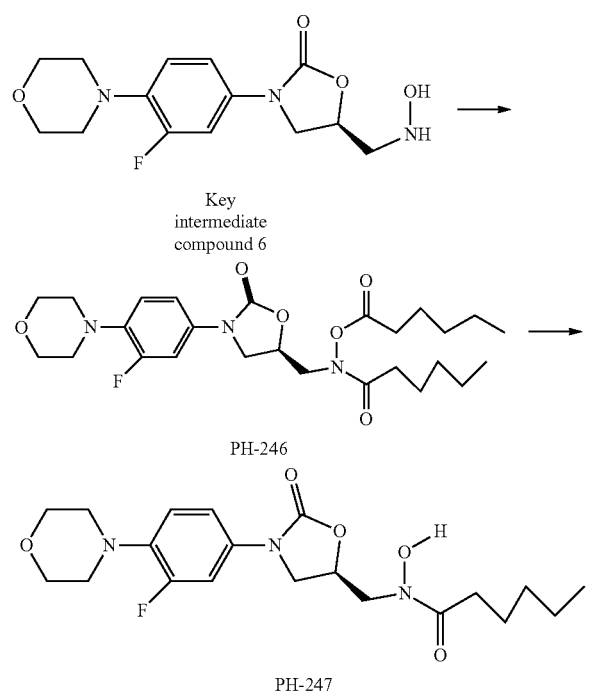

Compound PH-246 was prepared via the general procedure from the intermediate compound 6 (6.0 g, 19.27 mmol), hexanoyl chloride (8.08 mL, 57.82 mmol), triethylamine (16.20 mL; 115.64 mmol) in anhydrous DCM (90 mL) to give a crude product. Purification by silica gel column chromatography (EtOAc-Hexane, 1.3:2) gave the intermediate compound PH246, (R)—N-((3-(3-flouro-4-morpholinophenyl)methyl)-N-(hexanoyloxy)-hexanamide as a white solid 4.50 g, yield, 46%, m.p. 80-82.8° C. $^1$H-NMR (DMSO-d$_6$, 600 MHz): δ 7.48 (dd, 1H, J=2.5 Hz, 14.9 Hz, phenyl H), 7.18 (dd, 1H, J=2.3 Hz, 8.8 Hz, phenyl H), 7.06 (t, 1H, J=9.3 Hz, phenyl H), 4.84-4.88 (br. m, 1H, oxazolidinone H), 4.10-4.18 (br., 1H, oxazolidinone H, overlapping with oxazolidinone H triplet), 4.11 (t, 1H, J=9.0 Hz, oxazolidinone H, overlapping with the broad oxazolidinone H signal), 3.84-3.94 (br., 1H, methylene H), 3.74 (t, 5H, J=4.6 Hz, morpholine H and methylene H), 2.96 (t, 4H, J=4.6 Hz, morpholine H), 2.50 (br., 2H, methylene —CH$_2$— overlapping with DMSO signal), 2.10-2.28 (br., 2H, methylene H), 1.16-1.64 (m, 12H, methylene H), 0.82-0.88 (m, 6H, two methyl H). $^{13}$C-NMR (DMSO-d$_6$, 600 MHz): δ 155.30, 153.67, 153.53, 135.47, 133.30, 133.23, 119.18, 119.15, 114.10, 114.08, 106.72, 106.55, 70.09, 66.06, 50.62, 50.61, 47.11, 31.07, 30.94, 30.53, 30.40, 23.50, 21.68, 21.57, 13.64, 13.60. IR (KBr pellet, cm$^1$): v 2958, 2930, 2856, 1794, 1740, 1685, 1517, 1446, 1408, 1329, 1237, 1216, 1140, 1119, 1063. HRMS (m/z): Calcd for $C_{26}H_{38}FN_3O_6$: 507.2745, found 508.3000 (M$^+$+H), LRMS (m/z): 507.3 (M$^+$). Anal calcd for $C_{26}H_{38}FN_3O_6$: C: 61.52; H: 7.55; N: 8.28; found C: 61.44; H, 7.53; N, 7.95.

A solution of compound PH-246 (4.50 g, 8.87 mmol) in MeOH:THF (84 mL:21 mL) was treated with NaOH solution (709 mg in 20 mL water). Purification by recrystallization (EtOAc-hexane 2:1) gave the titled compound PH-247 as an off-white solid 3.23 g, yield, 89%, m.p. 118.5-120.5° C. $^1$H-NMR (DMSO-d$_6$, 600 MHz): δ 9.92 (s, 1H, N—OH, exchangeable with D$_2$O), 7.48 (dd, 1H, J=2.5 Hz, 15.0 Hz, phenyl H), 7.17 (dd, 1H, J=2.2 Hz, 8.8 Hz, phenyl H), 7.06 (t, 1H, J=9.4 Hz, phenyl H), 4.85-4.89 (br. m, 1H, oxazolidinone H), 4.12 (t, 1H, J=8.9 Hz, oxazolidinone H), 4.04 (dd, 1H, J=6.7 Hz, 14.7 Hz, oxazolidinone H), 3.73-3.76 (m, 5H, morpholine H and methylene H), 3.67 (dd, 1H, J=4.3 Hz, 14.8 Hz, methylene H), 2.96 (t, 4H, J=4.7 Hz, morpholine H), 2.35-2.38 (m, 2H, NCOCH$_2$CH$_2$CH$_2$CH$_2$CH$_3$), 1.45-1.49 (m, 2H, NCOCH$_2$CH$_2$CH$_2$CH$_2$CH$_3$), 1.22-1.30 (m, 4H, NCOCH$_2$CH$_2$CH$_2$CH$_2$CH$_3$), 0.85 (t, 3H, J=7.0 Hz, NCOCH$_2$CH$_2$CH$_2$CH$_2$CH$_3$). $^{13}$C-NMR (DMSO-d$_6$, 600 MHz): δ 173.90, 155.31, 153.88, 153.70, 135.49, 135.43, 133.41, 133.34, 119.18, 119.15, 114.07, 114.06, 106.71, 106.53, 69.86, 66.07, 50.64, 50.62, 50.26, 47.42, 31.46, 30.88, 23.70, 21.80, 13.71. IR (KBr pellet, cm$^{-1}$): v 3187, 2957, 2930, 2858, 1745, 1719, 1626, 1524, 1475, 1426, 1332, 1270, 1258, 1234, 1196, 1114, 1073. HRMS (m/z): Calcd for $C_{20}H_{28}FN_3O_5$: 409.2013, found 410.2000 (M$^+$+H), LRMS (m/z): 409.2 (M$^+$). Anal calcd for $C_{20}H_{28}FN_3O_5$: C: 58.67; H: 6.89; N: 10.26; found C: 58.32, H: 6.87, N: 10.61.

Compound PH-249: (R)—N-((3-(3-fluoro-4-morpholinophenyl)-2-oxooxazolidin-5-yl) methyl)-N-hydroxyheptanamide

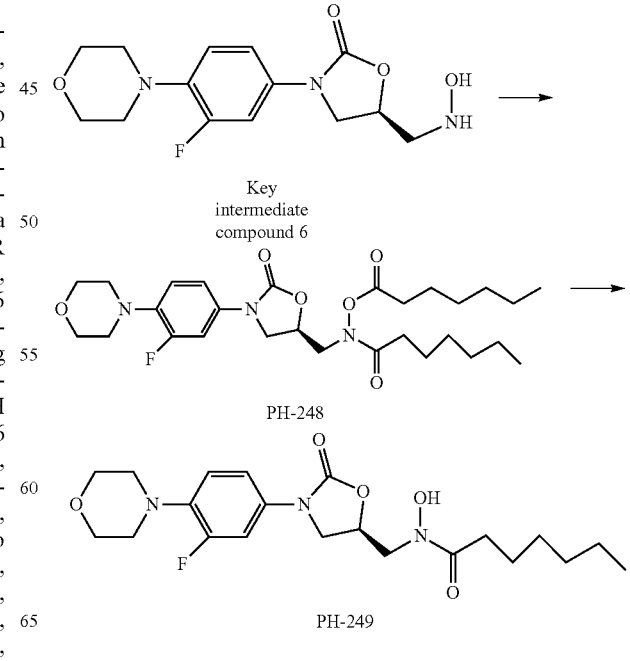

Compound PH-248 was prepared via the general procedure from the intermediate compound 6 (6.00 g, 19.27 mmol), heptanoyl chloride (8.95 mL, 57.81 mmol), triethylamine (16.21 mL; 115.62 mmol) in anhydrous DCM (30 mL) to give crude product. Purification by silica gel column chromatography (EtOAc-Hexane, 3:4) gave PH248, (R)—N-(3-(3-fluoro-4-morpholinophenyl)-2-oxooxazolidin-5-yl) methyl)-N-(heptanoyloxy) heptanamide as a white solid 6.82 g, yield, 66%, m.p. 68-70.5° C. $^1$H-NMR (DMSO-$d_6$, 600 MHz): δ 7.48 (dd, 1H, J=2.5 Hz, 14.7 Hz, phenyl H), 7.17 (dd, 1H, J=2.2 Hz, 8.8 Hz, phenyl H), 7.06 (t, 1H, J=9.3 Hz, phenyl H), 4.84-4.88 (br. m, 1H, oxazolidinone H), 4.10-4.18 (br., 1H, oxazolidinone H, overlapping with oxazolidinone H triplet), 4.11 (t, 1H, J=9.0 Hz, oxazolidinone H, overlapping with the broad oxazolidinone H signal), 3.84-3.94 (br., 1H, methylene H), 3.73 (t, 5H, J=4.6 Hz, morpholine H and methylene H), 2.96 (t, 4H, J=4.6 Hz, morpholine H), 2.50 (br., 2H, methylene —$CH_2$— overlapping with DMSO signal), 2.10-2.26 (br., 2H, methylene H), 1.15-1.64 (m, 16H, methylene H), 0.86-0.87 (m, 6H, two methyl H). $^{13}$C-NMR (DMSO-$d_6$, 600 MHz): δ 155.34, 153.72, 135.57, 135.51, 133.34, 133.27, 119.20, 119.17, 114.12, 114.10, 106.74, 106.57, 70.13, 66.10, 50.66, 50.65, 47.13, 31.03, 30.87, 30.74, 28.04, 27.94, 23.83, 21.87, 21.83, 13.79. IR (KBr pellet, cm$^1$): v 2960, 2929, 2855, 1794, 1740, 1685, 1519, 1446, 1410, 1329, 1236, 1217, 1140, 1119, 1066. HRMS (m/z): Calcd for $C_{28}H_{42}FN_3O_6$: 535.3058, found 535.3498 (M$^+$), LRMS (m/z): 535.4 (M$^+$). Anal calcd for $C_{28}H_{42}FN_3O_6$: C: 62.78; H: 7.90; N: 7.84; found C: 62.72; H, 7.90; N, 7.51.

A solution of the intermediate compound PH-248 (6.28 g, 11.72 mmol) in MeOH:THF (84 mL:21 mL) was treated with NaOH solution (928 mg in 20 mL water). Purification by recrystallization (EtOAc-hexane 2:1) gave the titled compound PH-249 as an off-white solid 4.30 g, yield, 87%, m.p. 123-125° C. $^1$H-NMR (DMSO-$d_6$, 600 MHz): δ 9.92 (s, 1H, N—OH, exchangeable with D$_2$O), 7.48 (dd, 1H, J=2.5 Hz, 14.9 Hz, phenyl H), 7.18 (dd, 1H, J=2.2 Hz, 8.8 Hz, phenyl H), 7.06 (t, 1H, J=9.3 Hz, phenyl H), 4.85-4.89 (br. m, 1H, oxazolidinone H), 4.12 (t, 1H, J=8.9 Hz, oxazolidinone H), 4.04 (dd, 1H, J=6.7 Hz, 14.7 Hz, oxazolidinone H), 3.73-3.75 (m, 5H, morpholine H and methylene H), 3.67 (dd, 1H, J=4.2 Hz, 14.9 Hz, methylene H), 2.96 (t, 4H, J=4.7 Hz, morpholine H), 2.35-2.38 (m, 2H, NCOCH$_2$CH$_2$CH$_2$CH$_2$CH$_2$CH$_3$), 1.44-1.49 (m, 2H, NCOCH$_2$CH$_2$CH$_2$CH$_2$CH$_2$CH$_3$), 1.21-1.27 (m, 6H, NCOCH$_2$CH$_2$CH$_2$CH$_2$CH$_2$CH$_3$), 0.85 (t, 3H, J=7.0 Hz, NCOCH$_2$CH$_2$CH$_2$CH$_2$CH$_2$CH$_3$). $^{13}$C-NMR (DMSO-$d_6$, 600 MHz): δ 173.93, 155.34, 153.92, 153.72, 135.51, 135.46, 133.44, 133.37, 119.20, 119.17, 114.08, 114.06, 106.71, 106.54, 69.90, 66.10, 50.67, 50.65, 50.27, 47.43, 31.54, 31.02, 28.36, 24.02, 21.91, 13.85. IR (KBr pellet, cm$^{-1}$): v 3188, 2957, 2923, 2855, 1743, 1719, 1626, 1525, 1473, 1426, 1332, 1271, 1235, 1196, 1115, 1073. HRMS (m/z): Calcd for $C_{21}H_{30}FN_3O_5$: 423.2169, found 424.2521 (M$^+$+H), LRMS (m/z): 423.3 (M$^+$). Anal calcd for $C_{21}H_{30}FN_3O_5$: C: 59.56; H: 7.14; N: 9.92; found C: 59.58, H: 7.52, N: 10.05.

Compound PH-251: (R)—N-((3-(3-fluoro-4-morpholinophenyl)-2-oxooxazolidin-5-yl) methyl)-N-hydroxyoctanamide

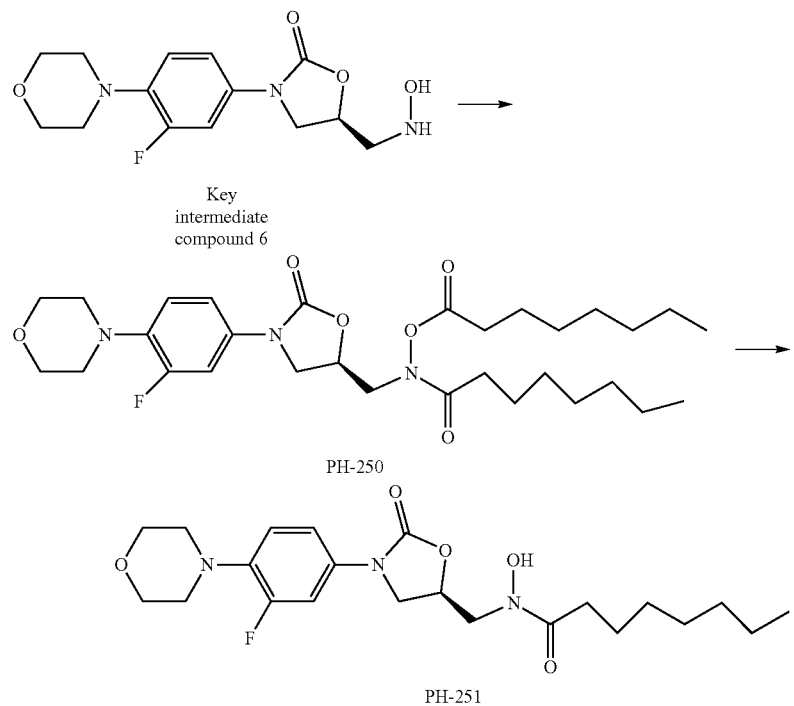

Compound PH-250 was prepared from the intermediate compound 6 (2.43 g, 7.80 mmol), octanoyl chloride (3.27 mL, 23.40 mmol), triethylamine (6.60 mL; 46.80 mmol) in anhydrous DCM (35 mL) to give crude product. Purification by silica gel column chromatography (EtOAc-Hexane, 1:2; 3:4) gave the intermediate compound PH-250, (R)—N-((3-(-Fluoro-4-morpholino-phenyl)-2-oxooxazolidin-5-yl) methyl)-N-(octanoyloxy)octanamide as a white solid 2.20 g, yield, 50%, m.p. 49-53° C. $^1$H-NMR (DMSO-$d_6$, 600 MHz):

δ 7.48 (dd, 1H, J=2.5 Hz, 14.9 Hz, phenyl H), 7.17 (dd, 1H, J=2.3 Hz, 8.8 Hz, phenyl H), 7.06 (t, 1H, J=9.3 Hz, phenyl H), 4.84-4.88 (br. m, 1H, oxazolidinone H), 4.09-4.18 (br., 1H, oxazolidinone H, overlapping with oxazolidinone H triplet), 4.11 (t, 1H, J=9.1 Hz, oxazolidinone H, overlapping with the broad oxazolidinone H signal), 3.84-3.94 (br., 1H, methylene H), 3.73 (t, 5H, J=4.6 Hz, morpholine H and methylene H), 2.96 (t, 4H, J=4.6 Hz, morpholine H), 2.50 (br., 2H, methylene —$CH_2$— overlapping with DMSO signal), 2.10-2.24 (br., 2H, methylene H), 1.20-1.64 (m, 20H, methylene H), 0.83-0.87 (m, 6H, two methyl H). $^{13}$C-NMR (DMSO-$d_6$, 600 MHz): δ 155.33, 153.72, 135.56, 135.50, 133.34, 133.28, 119.19, 119.16, 114.09, 114.07, 106.71, 106.54, 70.14, 66.10, 50.66, 50.65, 47.11, 31.07, 31.03, 28.34, 28.33, 28.25, 28.23, 23.89, 21.97, 13.86. IR (KBr pellet, $cm^{-1}$): ν 2954, 2925, 2853, 1790, 1750, 1673, 1520, 1442, 1417, 1377, 1328, 1272, 1225, 1193, 1120, 1075. HRMS (m/z): Calcd for $C_{30}H_{46}FN_3O_6$: 563.3371, found 564.3386 ($M^+$+H), LRMS (m/z): 563.3 ($M^+$). Anal calcd for $C_{30}H_{46}FN_3O_6$: C: 63.92; H: 8.23; N: 7.45; found C: 64.01; H, 8.26; N, 7.43.

A solution of the intermediate compound PH-250 (2.15 g, 3.81 mmol) in MeOH:THF (56 mL:14 mL) was treated with NaOH solution (305 mg in 20 mL water). Purification by recrystallization (EtOAc-hexane 2:1) gave the titled compound PH-251 as an off-white solid 1.30 g, yield, 78%, m.p. 119-122° C. $^1$H-NMR (DMSO-$d_6$, 600 MHz): δ 9.93 (s, 1H, N—OH, exchangeable with $D_2O$), 7.48 (dd, 1H, J=2.5 Hz, 14.9 Hz, phenyl H), 7.17 (dd, 1H, J=2.2 Hz, 8.8 Hz, phenyl H), 7.06 (t, 1H, J=9.4 Hz, phenyl H), 4.85-4.89 (br. m, 1H, oxazolidinone H), 4.12 (t, 1H, J=8.9 Hz, oxazolidinone H), 4.04 (dd, 1H, J=6.7 Hz, 14.7 Hz, oxazolidinone H), 3.73-3.75 (m, 5H, morpholine H and methylene H), 3.67 (dd, 1H, J=4.2 Hz, 14.9 Hz, methylene H), 2.96 (t, 4H, J=4.6 Hz, morpholine H), 2.34-2.38 (m, 2H, $NCOCH_2CH_2CH_2CH_2CH_2CH_2CH_3$), 1.44-1.50 (m, 2H, $NCOCH_2CH_2CH_2CH_2CH_2CH_2CH_3$), 1.18-1.30 (m, 8H, $NCOCH_2CH_2CH_2CH_2CH_2CH_2CH_3$), 0.85 (t, 3H, J=7.0 Hz, $NCOCH_2CH_2CH_2CH_2CH_2CH_2CH_3$). $^{13}$C-NMR (DMSO-$d_6$, 600 MHz): δ 173.96, 155.36, 153.95, 153.75, 135.54, 135.48, 133.46, 133.40, 119.22, 119.19, 114.09, 114.07, 106.72, 106.55, 69.94, 66.13, 50.69, 50.68, 50.26, 47.44, 31.57, 31.14, 28.70, 28.49, 24.10, 22.04, 13.93. IR (KBr pellet, $cm^{-1}$): ν 3184, 2956, 2923, 2854, 1743, 1720, 1626, 1524, 1471, 1446, 1427, 1332, 1272, 1235, 1197, 1115, 1075. HRMS (m/z): Calcd for $C_{22}H_{32}FN_3O_5$: 437.2326, found 438.2402 ($M^+$+H), LRMS (m/z): 437.2 ($M^+$). Anal calcd for $C_{22}H_{32}FN_3O_5$: C: 60.40; H: 7.37; N: 9.60; found C: 60.54, H: 7.10, N: 9.43.

Example 3

Evaluation of Biological Activities of Oxazolidinone Hydroxamic Acid Derivatives Methodology (In Vitro Inhibition of $LTB_4$ generation from human whole blood: All compounds were evaluated for inhibitory activity against 5-LO-dependent generation of leukotriene $B_4$ ($LTB_4$) from activated human whole blood. With ethical approval from the Health Sciences Center Ethical Committee of Kuwait University, heparinized fresh human blood samples from apparently healthy individuals were obtained from the Kuwait Central Blood Bank. Aliquots of 185 μl of whole blood were dispensed into each well of 96-well culture plate containing 5 μl of the priming agent, lipopolysaccharide (LPS) at a final concentration of 1 μg/ml. After a 15 min incubation at 37° C., 5 μl aliquots of the test compounds (0.001-30 μM) or the reference drug, zileuton (as positive control) or the vehicle (0.05% DMSO), were added. After further incubation for 15 min at 37° C., 5 μl of N-formyl-methionyl-leucyl-phenylalanine (FMLP), at 1 M final concentration, was added to stimulate LT production. The reaction was stopped after 15 min, and the supernatants recovered by centrifugation and stored at −40° C. pending analysis of the $LTB_4$ content.

Inhibition of $LTC_4$ release from isolated human monocytes: Mononuclear cells were first isolated from heparinized fresh blood using the Ficoll-Hypaque gradient centrifugation method. Monocytes were subsequently purified by adherence to plastic according to standard protocols. The purity of the adherent monocytes (CD14+) was routinely confirmed by flow cytometry to be >95% and viability (by trypan blue exclusion method) was routinely >97%. Adherent monocytes were then washed and incubated in 190 μl culture medium RPMI-1640 supplemented with 100 U/ml penicillin, 100 μg/ml streptomycin and 10% heat-inactivated fetal bovine serum (Sigma-Aldrich, St Louis, Mo., USA). Cells were then incubated with the various test compounds (0.01-30 μM) or vehicle (0.05% DMSO) or zileuton (positive control) for 15 min before being stimulated with 5 μl of the calcium ionophore A23187 at a final concentration of 2.5 μM. After a further incubation for 15 min, the culture supernatants were recovered by centrifugation and stored at −40° C. pending $LTC_4$ determination.

Inhibition of $LTC_4$ release and degranulation in allergen/IgE-activated bone marrow-derived mouse mast cells (BMMC): Bone marrow-derived mast cells (BMMC) were generated from pathogen-free 5-7 week old male Balb/c mice according to the method of Davis et al., [2004] (Davis, B. J., et al., (2004), *Journal of Immunology*, 173: 6914-6920). Essentially, bone marrow cells were obtained by flushing of the femoral bone marrow and cultured in RPMI 1640 medium supplemented with 10% FBS, 100 U/ml penicillin, and 100 μg/ml streptomycin, 25 mM HEPES, 1.0 mM sodium pyruvate, 0.1 mM nonessential amino acids, 0.0035% 2-mercaptoethanol, and 30 ng/ml mouse recombinant IL-3, with culture medium replaced every two days. Cells were used after 4-8 weeks of culture, by which time at least 97% of the cells would have differentiated into mast cells.

The generated BMMCs were seeded at $5 \times 10^4$ cells/well in a 96-well flat-bottom culture plate and passively sensitized overnight with 0.5 μg/ml anti-DNP monoclonal IgE antibody (clone SPE-7, Sigma-Aldrich, St. Louis, Mo., USA). The cells were then washed twice to remove any unbound antibody and subsequently re-suspended in reaction buffer (135 mM NaCl, 5 mM KCl, 1.8 mM $CaCl_2$), 1 mM $MgCl_2$, 5.6 mM glucose, 0.05% BSA and 20 mM HEPES, pH 7.4). They were then pre-incubated with the test compounds (0.01-30 μM) or the solvent (0.05% DMSO) for 15 min before being stimulated with the specific antigen, DNP-BSA (30 ng/ml). After 30 min incubation at 37° C., the amount of $LTC_4$ released into the supernatant (as index of 5-LO activity) was determined by ELISA as described below.

The concurrently-released granular enzyme, β-hexoseaminidase (as index of degranulation) was determined as described below.

Assay of released leukotrienes/β-hexoseaminidase enzyme: Appropriately diluted supernatants were assayed for the released LTs ($LTB_4$ and $LTC_4$), by the enzyme immunoassay (EIA) method using assay kits supplied by R&D Systems (Minneapolis, Minn., USA) and following the manufacturer's instructions.

The beta-hexoseaminidase released into the supernatant by the degranulating BMMCs was determined colorimetrically using p-nitrophenyl-N-acetyl-β-D-glucosaminide as substrate. Briefly, 50 l of sample was mixed with 50 l of the substrate (5 mM in 0.2 M citrate buffer, pH 4.5) and incubated at 37° C. for 1 h. The absorbance of the colored product (p-nitrophenol) was then read at 405 nm in a microplate reader. Results were expressed as percentage of the total cell content (determined in cells lysed with 0.1% triton-x-100).

Evaluation of direct 5-LO inhibitory activity in a cell-free assay: The assay was based on the oxidation of the dye 2',7'-dichlorodihydrofluorescein diacetate (H2DCF-DA) to a highly fluorescent product by 5-LO enzymatic products, specifically as described in Pufahl et al., 2007 (Pufahl, R. A., et al. (2007). Analytical biochemistry, 364(2), 204-212). H2DCF-DA (60 µM) was first pre-cleaved by incubating with 450 mU/ml recombinant human 5-LO enzyme in Tris buffer (containing 50 mM Tris, pH=7.5, 2 mM EDTA, 2 mM $CaCl_2$), 1 mM dithiothreitol (DTT) and 0.6 U/ml glutathione peroxidase) for 10 min at room temperature. Then, to each well of a black 96-well plate was added 25 µl of the above enzyme/dye solution, followed by 25 µl of the test compounds or zileuton (0.01-30 µM) or drug vehicle, in duplicates. After 10 min incubation at room temperature, the reaction was started with the addition of 50 µl of the substrate solution (Tris buffer containing 20 µM ATP and 20 µM arachidonic acid). After a further 20 min, the reaction was terminated with 100 µl acetonitrile. Fluorescence was read at 500 nm excitation and 520 emission, with Novostar® microplate reader (BMG Labtech, Offenburg, Germany). Appropriate controls, including 100 µM nordihydroguaiaretic acid (NDGA), were included to isolate only the 5-LO-attributable, NDGA-inhibitable RFU values.

In Vitro Toxicity Testing: Adherent human monocytes, prepared as described above, were used. The cells were cultured with various concentrations of the test compounds or vehicle, or with 0.05% Triton-X as positive control for 3 h or 24 h. At the end of the culture, cell viability was determined using the MTT (3-(4,5 dimethylthiazol-2-yl)-2, 5-diphenyltetrazolium bromide) assay method. Briefly, 15 µl of the MTT solution (5 mg/ml) was added to each well, and incubated at 37° C. for 4 h. After removing the supernatant, 200 µl of dimethylsulfoxide (DMSO) was added to dissolve the crystals. Absorbance at 570 nm was then measured in a microplate reader. Viability was expressed as percentage of the vehicle-treated cells.

Methodology (In Vivo)

Inhibition of zymosan-induced peritoneal inflammation in mice: Female Balb/c mice, 6-8 weeks old, obtained from the Animal Resources Center of the Health Sciences Center, Kuwait University, were used. They were maintained under temperature-controlled conditions with an artificial 12-h light/dark cycle and allowed standard chow and water ad libitum. The study protocol was approved by the "Health Sciences Center Animal Welfare Committee" and complied with the "Guidelines for the Care and Use of Laboratory Animals" of the Health Sciences Centre, Kuwait University.

The zymosan-induced peritonitis model—a recognized LT-mediated inflammatory reaction, described particularly in Hanke et al., 2013 (Hanke, T., et al. (2013). *Journal of medicinal chemistry,* 56(22), 9031-9044) was used. Five groups of mice, 8-12 per group, were treated subcutaneously with either the test compounds PH-251 and PH-249 (the most active compounds) at doses of 3-30 mg/kg or drug vehicle (4% DMSO/67.2% PEG/28.8% PBS) alone or zileuton for comparison. After 30 min, all groups were injected intraperitonally with 0.2 ml of activated zymosan (2 mg/ml) except the control group that received 0.2 ml PBS. After 2 h, all animals were killed and the peritoneal exudate was collected by washing the cavity with 3 ml of heparinized (10 IU/ml) PBS. Cells in the exudate were recovered by centrifugation and counted in a hemocytometer while the supernatant volume was recorded and then stored and frozen at −78° C. until used for the determination of $LTC_4$ by ELISA, as detailed above.

Inhibition of allergen-induced Airway hyperresponsiveness (AHR) and inflammation in mouse model of asthma; Immunization, challenge and drug treatment: Female mice, as specified above, were immunized intraperitoneally (i.p.) with 10 µg ovalbumin mixed with 0.2 ml of aluminum hydroxide gel (Alu-Gel-S; SERVA Electrophoresis GmbH, Heidelberg, Germany), on day 0 and repeated on day 7. On day 14, after the start of immunization, the animals were challenged intra-nasally, once a day for 4 consecutive days, with 50 µl of 0.06% ovalbumin solution in PBS. Control animals were similarly immunized with PBS and challenged intra-nasally with 50 µl PBS. All intra-nasal administrations were done following light anesthesia with halothane.

The animals were divided into 5 groups A-E (10-14 animals per group). Mice in groups A and B were pre-treated subcutaneously with the drug vehicle (4% DMSO/67.2% PEG/28.8% PBS) 1 h before and 1 h after each intra-nasal challenge with PBS and ovalbumin, respectively. In the same manner, groups C and D were pre-treated with PH-251 at 15 mg/kg and 30 mg/kg, respectively, and group E with dexamethasone (3 mg/kg), 1 h before and 1 h after each intra-nasal challenge with ovalbumin.

Different treatment groups were used for the AHR and cytology/histology studies. Twenty four hours after the last intra-nasal challenge/drug treatment, lung function was measured in some animals while in others bronchoalveolar lavage (BAL), cytology and histology were performed after they were sacrificed with overdose of halothane.

Measurement of AHR: AHR was measured in individual mice using a Finepoint Series RC site (Buxco Research Systems, Wilmington, N.C., USA), according to the manufacturer's guidelines. In short, mice were anesthetized with an i.p. injection of ketamine/xylazine (1 mg/kg:0.1 mg/kg) cocktail and tracheotomized with a steel 18-gauge cannula. Mice were subsequently mechanically ventilated at a rate of 150 breaths/min, and tidal volume of 0.15 ml, using a computerized small animal ventilator (Finepoint; Buxco Electronics, Wilmington, N.C., USA) as previously described in El-Hashim et al., 2011b (El-Hashim, A. Z., et al. (2011). *Life sciences,* 89(11-12), 378-387). After 5 min. of stabilization followed by administration of PBS, airway resistance was measured by exposing mice to aerosolized methacholine (6.25-50.0 mg/ml) (5 l per delivery) delivered by nebulizer administration, and reported as percentage change in lung resistance ($R_L$).

Statistical Analysis: All data were analyzed using Graph-Pad Prism software (GraphPad Software, San Diego, Calif., U.S.A.). The $IC_{50}$ values were calculated from the concentration-response curves by non-linear regression analysis (normalized variable). Differences between experimental groups were first analyzed by one-way ANOVA, followed by Bonferroni's post-hoc test. In some cases, statistical analysis was done be the One Sample t-test as appropriate. A p-value of less than 0.05 was taken as statistically significant. For the AHR, data were expressed as percentage of baseline value for each animal and the area under the dose response curve (AUC) values for the different groups were then tested for statistical significance as stated above.

Results

The exemplary synthesized oxazolidinone hydroxamic acid derivatives were tested for inhibitory activity against leukotriene (LT) biosynthesis in 4 in vitro test systems—human whole blood, isolated human blood monocytes, $LTC_4$ release from IgE/allergen-activated mouse mast cells, and for direct effect on the activity of recombinant human 5-LO enzyme.

In each test system, the inhibitory potencies [expressed as 50% inhibitory concentration ($IC_{50}$) values] of the compounds were compared with those of the reference drug, zileuton—the only clinically available 5-LO inhibitor.

As shown in Table 1 below, most of the 15 representative compounds presented had good ($IC_{50}$<10 μM) to excellent ($IC_{50}$<1 μM) inhibitory activity in at least two of the test systems. The most active compounds (PH-211, PH-239, PH-241, PH-247, PH-249 and PH-251) were active in all four test systems. In many cases the inhibitory activities of the compounds were comparable or better than those of zileuton. For example, on human whole blood and isolated human monocytes, compound PH-249 ($IC_{50}$=0.7 μM and 0.9 μM, respectively) had potencies for the inhibition of LT release that were similar to those of zileuton ($IC_{50}$=0.7 μM and 0.5 μM, respectively), whereas, on mast cells activated by an allergic mechanism, compound PH-251 had an outstanding potency ($IC_{50}$=0.2 μM), which was better than that of zileuton ($IC_{50}$=0.4 μM).

PH-251, which were the most active in directly inhibiting 5-LO, in the cell-free system were also the most active in inhibiting LT biosynthesis in cell-based systems. These results show that the mechanism of inhibition of LT biosynthesis by these compounds is by direct inhibition of 5-LO, and that their potencies are comparable to that of zileuton.

From these results, it can be concluded that the oxazolidinone hydroxamic acid derivatives are very active inhibitors of 5-LO, affecting cells of both humans and mice. Their action is independent of the mode of cell activation, as they equally affect cells activated by LPS/FMLP, calcium ionophore and antigen-antibody immune complex. These findings show that the compounds have the potential of being useful not only in allergic diseases, such as asthma, allergic rhinitis, atopic dermatitis, but also in many other inflammatory diseases in which LTs, induced by a variety of stimuli, are known to be involved.

Figure 2A:
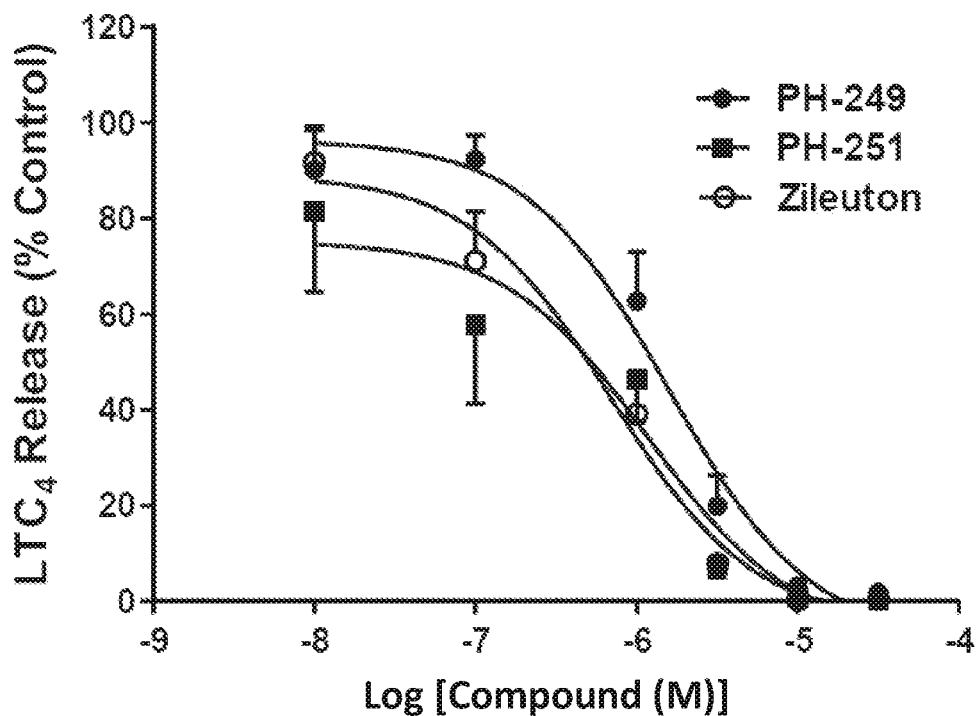
FIG. 2A is a graph depicting evidence of the inhibitory effect of representative compounds (PH-249 and PH-251) in comparison with Zileuton on $LTC_4$ release.
Figure 2B:
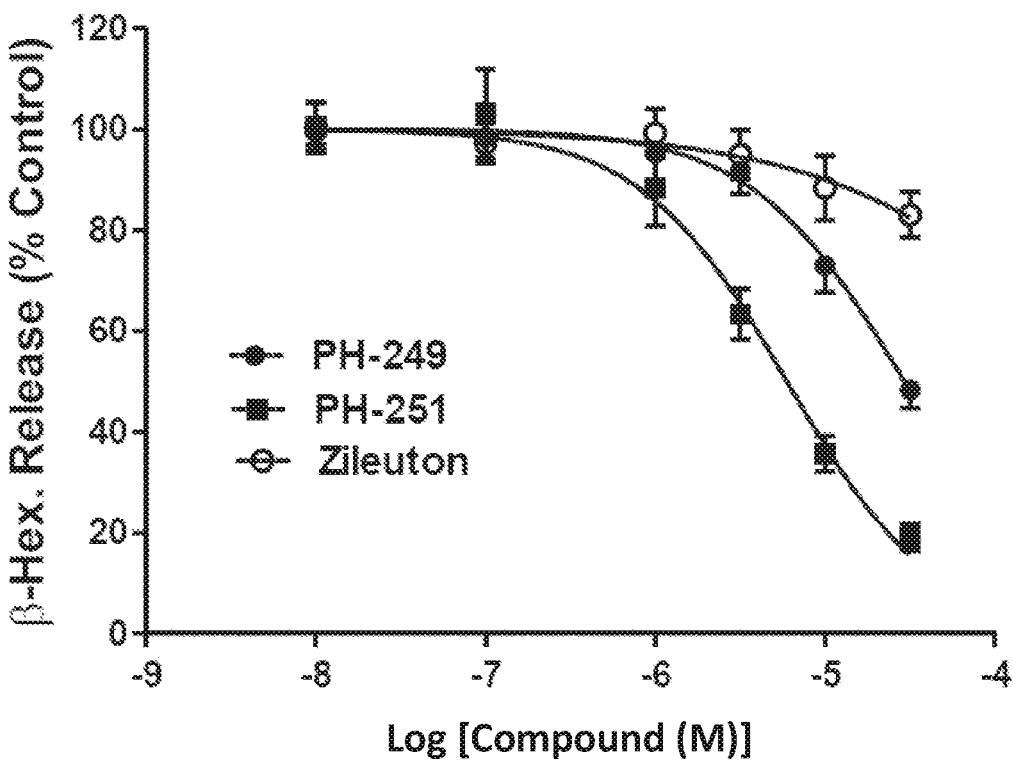
FIG. 2B is a graph depicting the effect of representative compounds (PH-249 and PH-251) on degranulation (release of granular β-hexoseaminidase) in activated bone marrow-derived mouse mast cells.

In addition to the inhibition of LT release, the exemplary compounds displayed strong inhibitory activity against mast cell degranulation—a property that is completely lacking in existing 5-LO inhibitors. FIGS. 2A-2B shows the inhibitory effects of representative compounds (PH-249 and PH-251) in comparison with zileuton on $LTC_4$ release (FIG. 2A) and degranulation (release of granular β-hexoseaminidase) (FIG. 2B), in activated bone marrow-derived mouse mast cells. Cells were passively sensitized with 0.5 μg/ml mouse monoclonal anti-DNP IgE overnight, washed and pre-incu-

TABLE 1

Inhibitory activity of some oxazolidinone hydroxamate derivatives on human 5-LO activity and on the biosynthesis of 5-lipoxygenase products in human whole blood, human isolated monocytes and IgE/antigen-activated mouse mast cells.

| SN | Compd Code | $R_1$ | $R_2$ | Human recomb. 5-LO | Human whole blood $LTB_4$ | Human monocyte $LTC_4$ | Mouse mast cell $LTC_4$ |
|---|---|---|---|---|---|---|---|
| 1 | PH-238 | H | $NH_2$ | 14.7 | 7.9 | 30.7 | 23.8 |
| 2 | PH-23 | H | methyl | >30 | 3.3 | 18.7 | 20.7 |
| 3 | PH-199 | H | ethyl | 11.8 | 1.4 | 8.2 | 6.3 |
| 4 | PH-204 | Isopropyl-carbonyl | isopropyl | >30 | 10.7 | >50 | 21.8 |
| 5 | PH-205 | H | isopropyl | 3.9 | 2.3 | 14.1 | 13.8 |
| 6 | PH-206 | Cyclopropyl-carbonyl | cyclopropyl | >30 | 7.9 | >50 | 37.3 |
| 7 | PH-211 | H | cyclopropyl | 3.5 | 1.3 | 7.5 | 8.7 |
| 8 | PH-239 | H | isobutyl | 4.7 | 3.5 | 8.0 | 3.1 |
| 9 | PH-241 | H | butyl | 3.3 | 2.2 | 3.2 | 2.8 |
| 10 | PH-245 | H | cyclobutyl | ND | 3.4 | ND | ND |
| 11 | PH-244 | H | cyclopentyl | ND | 5.5 | ND | ND |
| 12 | PH-246 | Hexanoyl | pentyl | 21.6 | 1.5 | 7.1 | 3.3 |
| 13 | PH-247 | H | pentyl | 3.4 | 2.3 | 2.5 | 2.9 |
| 14 | PH-249 | H | hexyl | 1.9 | 0.7 | 0.9 | 1.3 |
| 15 | PH-251 | H | heptyl | 1.6 | 1.9 | 2.4 | 0.2 |
| | Zileuton | | | 0.8 | 0.7 | 0.5 | 0.4 |

Results from cell-free studies using human recombinant 5-LO protein (Table 1) showed that the inhibitory effect of the compounds, in general, paralleled their effects in cell-based assays. For example, compounds PH-249 and bated with the compounds or vehicle for 15 min. before stimulation for a further 30 min. with the specific antigen DNP-BSA (30 ng/ml). The supernatants were then analyzed for $LTC_4$ and β-hexoseaminidase and concurrently released.

As shown in FIGS. 2A-2B, while both zileuton and two representative compounds (PH-251 and PH-249) were equally effective in inhibiting the generation of LTC4 from IgE/allergen-activated mast cells (FIG. 2A), only the representative compounds were able to inhibit degranulation (FIG. 2B).

Figure 3A:
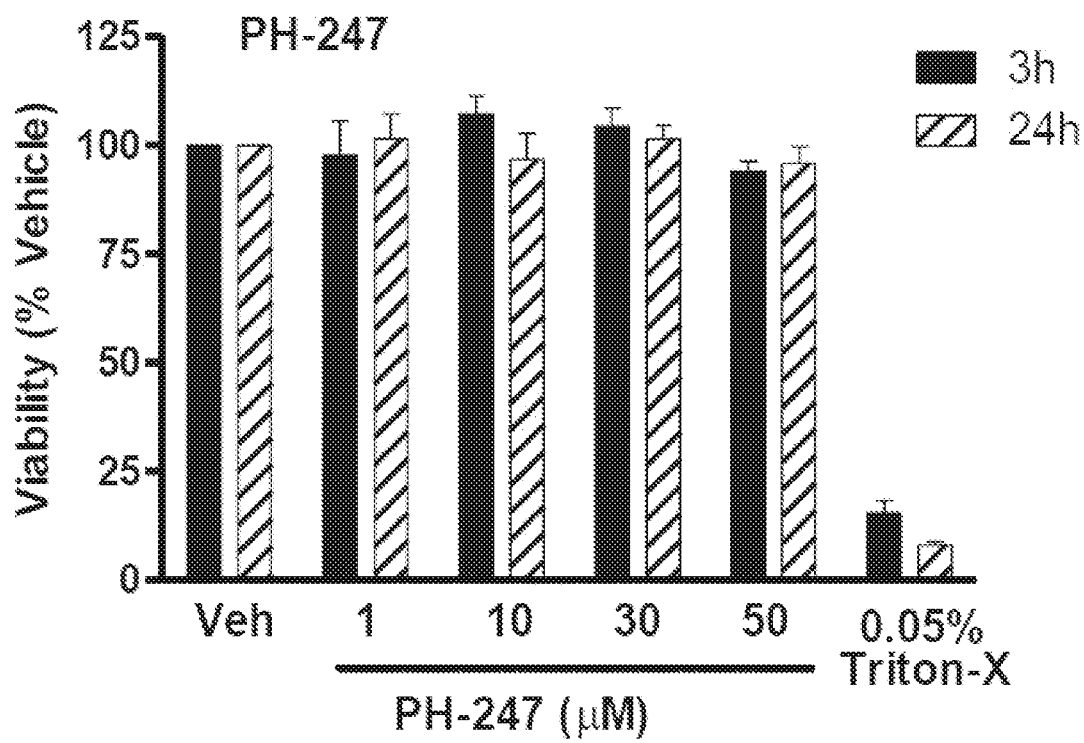
FIG. 3A is a graph depicting the effect of representative compound PH-247 on the viability of isolated human monocytes.
Figure 3B:
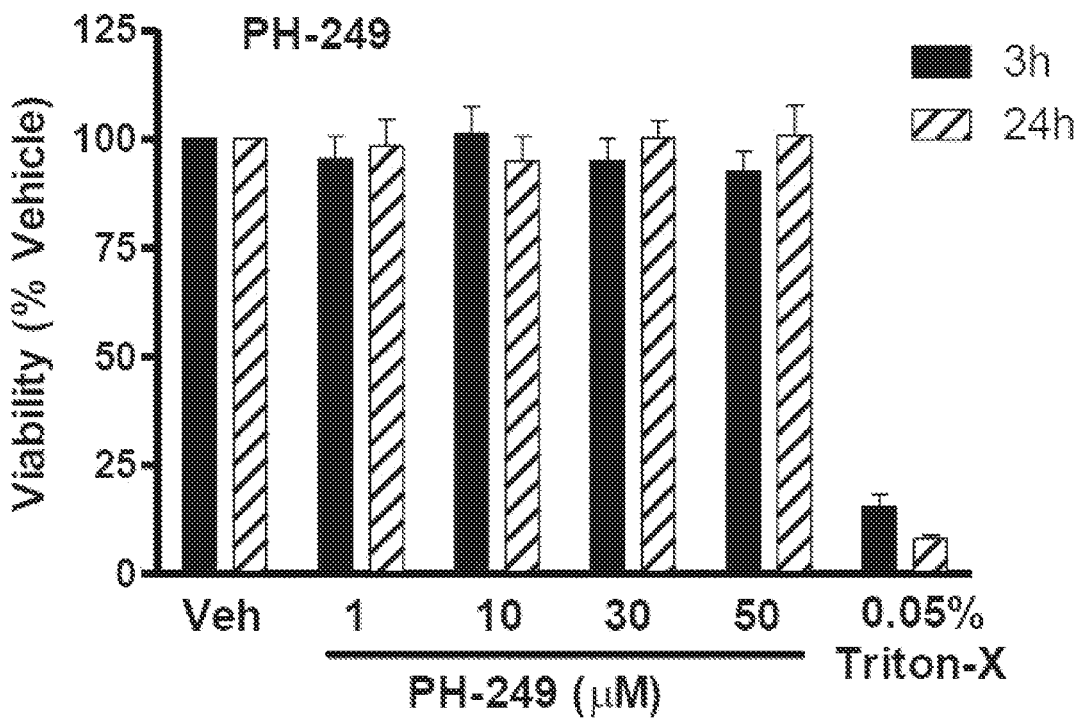
FIG. 3B is a graph depicting the effect of representative compound PH-249 on the viability of isolated human monocytes.

In order to exclude the possibility that the in vitro inhibitory activity of the exemplary compounds was a result of direct toxicity of the compound on the cells, the effect of representative compounds (PH-247 and PH-249) on the viability of isolated human monocytes after 3 h and 24 h treatment was tested (FIGS. 3A-3B). Cells were exposed to the test compounds or triton-X (as a positive control), for 3 h or 24 h, and thereafter viability was assessed by the MTT method, n=3. As shown in FIGS. 3A-3B, at concentrations up to 50 µM (a concentration far beyond that required for 100% inhibition of LT release), no significant effect on cell viability was detected for either exemplary compound, whether cells were cultured with the exemplary compound for 3 h or 24 h. This shows that the compounds are not cytotoxic.

To determine if the compounds are active in vivo, representative compounds PH-249 and PH-251 were tested in two animal models of disease—zymosan-induced mouse peritonitis and mouse asthma model—both of which are well-known models in which LTs are known to play a critical role, as disclosed, for example in Hanke et al., 2013 (Hanke, T., et al., (2013). *Journal of Medicinal Chemistry*, 56: 9031-9044) and Eum et al., 2003 (Eum, S. Y., et al. (2003). *American journal of respiratory cell and molecular biology*, 28(1), 25-32).

As shown in Table 2, intra-peritoneal administration of zymosan (plus drug vehicle) resulted in significant inflammatory response characterized by increases in volume, cellular infiltration and $LTC_4$ content of the peritoneal fluid recovered after 2 h.

TABLE 2

In vivo inhibitory effect of representative compounds - PH-249 and PH-251, on zymosan-induced peritoneal inflammation in mice.

| Group/ Treatment | Total $LTC_4$ (ng) | Total Cell No ($\times 10^6$) | Net Exudate Vol (ml) | N |
|---|---|---|---|---|
| PBS/Veh | 50.3 ± 6.3 | 12.5 ± 2.6 | 0.01 ± 0.01 | 12 |
| Zymo/Veh | 262.5 ± 40.3### | 36.8 ± 3.8### | 0.41 ± 0.14### | 12 |
| Zymo/PH-251 (3 mg/kg) | 101.7 ± 20.2*** | 21.1 ± 1.6** | 0.24 ± 0.05 | 6-8 |
| Zymo/PH-251 (10 mg/kg) | 77.4 ± 16.8*** | 16.4 ±17*** | 0.12 ± 0.08 | 6-8 |
| Zymo/PH-251 (30 mg/kg) | 33.9 ± 4.9*** | 17.6 ± 2.1** | 0.04 ± 0.02* | 6-8 |
| Zymo/PH-249 (10 mg/kg) | 107.2 ± 51.6** | 39.7 ± 6.6 | 0.16 ± 0.08 | 7 |
| Zymo/PH-249 (30 mg/kg) | 102.8 ± 20.9*** | 17.8 ± 2.2** | 0.06 ± 0.01* | 7 |
| Zymo/Zil (10 mg/kg) | 97.2 ± 47.3*** | 24.9 ± 2.1 | 0.20 ± 0.07 | 6-8 |
| Zymo/Zil (3 mg/kg) | 71.0 ± 12.4*** | 16.7 ± 2.8** | 0.14 ± 0.04 | 6-8 |
| Zymo/Zil (30 mg/kg) | 48.3 ± 9.8*** | 19.1 ± 4.4** | 0.10 ± 0.05 | 6-8 |

$p < 0.01$ (with respect to PBS/Veh);
*$p < 0.5$,
**$p < 0.01$,
***$p < 0.001$ (with respect to Zymo/Veh)

Pretreatment with the two compounds (3 mg/kg-30 mg/kg) resulted in a highly significant and dose-dependent inhibition of total $LTC_4$ content and cellular accumulation in the lavage fluid ($p<0.01$ or $p<0.001$), but for the exudate volume, only the inhibition by the higher dose reached statistical significance, $p<0.05$. In general, the effects were comparable to those of zileuton except that the latter had no significant effect on exudate volume even at the high dose of 30 mg/kg.

Figure 4A:
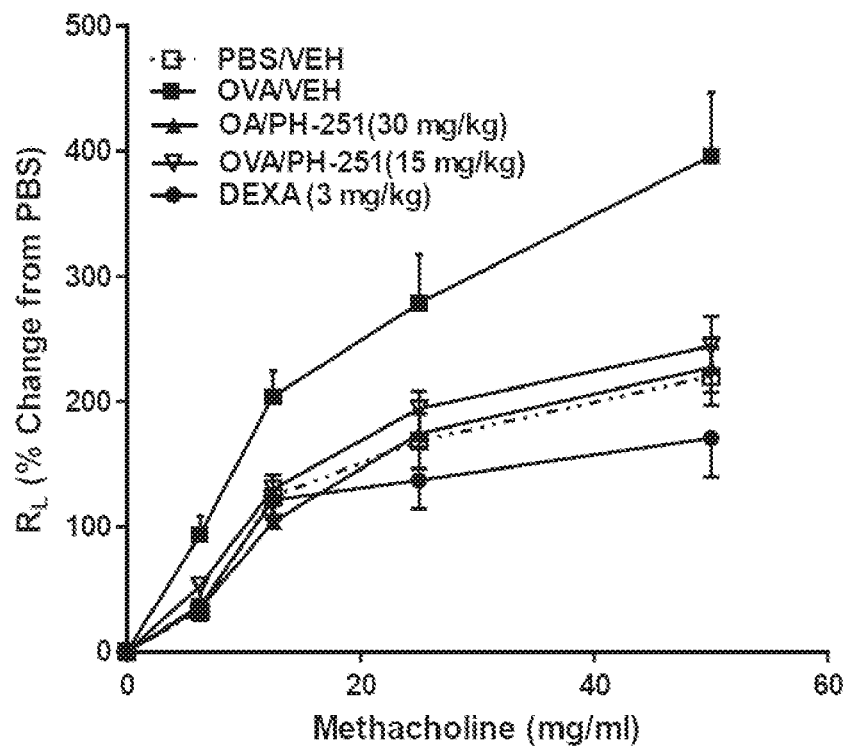
FIG. 4A depicts dose response curves showing in vivo inhibitory effects of representative compound PH-251 and various controls on airway hyper-responsiveness (AHR) in a mouse model of asthma.
Figure 4B:
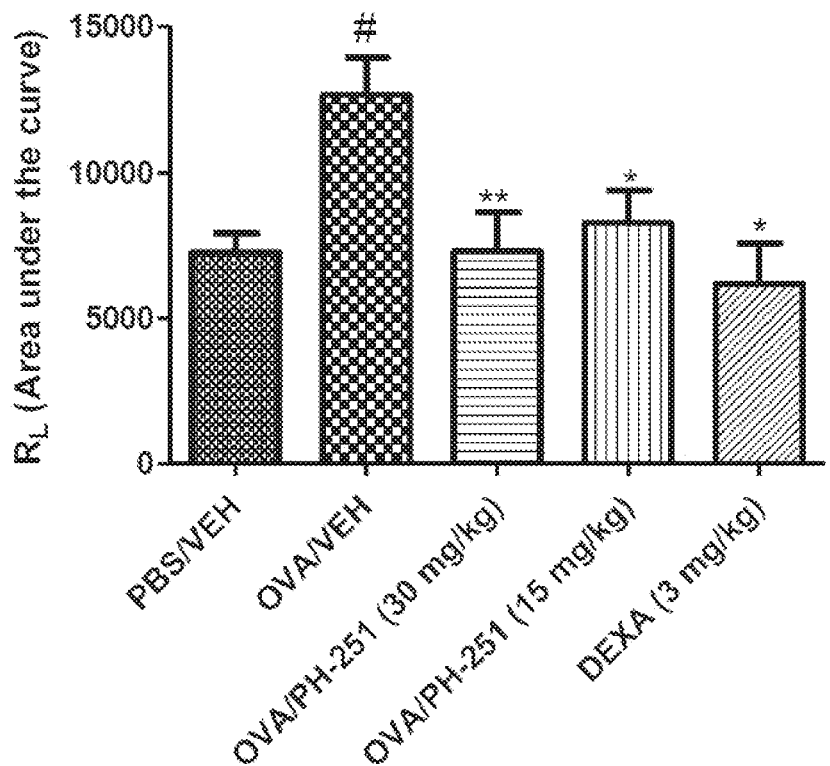
FIG. 4B shows the corresponding areas under the curves depicted in FIG. 4A.

In the mouse asthma model—a disease model very similar to human asthma, the representative compound, PH-251 (15 or 30 mg/kg), was tested for the ability to protect the animals from the development of antigen-induced airway hyperresponsiveness (AHR)—a hallmark of allergic airway inflammation. As shown in FIGS. 4A-4B, both tested doses of the representative compound, administered during the antigen challenge phase, almost completely abolished the development of AHR to inhaled methacholine. The effect was comparable to that produced by the standard drug dexamethasone (3 mg/kg).

These results show that the oxazolidinone hydroxamic acid derivatives have useful in vivo biological activities in animal models of asthma and inflammation and therefore have strong potential for development into drugs for the treatment of human allergic diseases (including asthma), as well as inflammatory diseases in general. Since IgE/allergen-dependent activation of mast cells and their consequent degranulation and release of LTs constitute the basis of all allergic diseases, the ability of the exemplary compounds to inhibit both 5-LO activity and degranulation of mast cells gives them strong potential therapeutic advantage over existing 5-LO inhibitors that lack this additional effect. The oxazolidinone hydroxamic acid derivatives therefore have a high potential as drugs for the treatment of allergic and inflammatory diseases.

It is to be understood that the oxazolidinone hydroxamic acid derivatives useful for treating allergies or inflammatory diseases are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A compound having the formula:

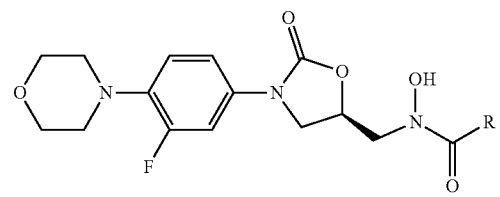

wherein
R is selected from the group consisting of pentyl, hexyl, and heptyl,
or a pharmaceutically acceptable salt thereof.

2. The compound of claim 1, wherein R is selected from the group consisting of hexyl and heptyl.

3. A pharmaceutical composition comprising a therapeutically effective amount of the compound of claim 1 and a pharmaceutically acceptable carrier.

4. A method of treating a subject suffering from at least one disease selected from the group consisting of an allergic disease and an inflammatory disease, comprising administering to the subject in need thereof a therapeutically effective amount of a compound of claim 1.

5. The method of claim 4, wherein the compound inhibits 5-lipoxgygenase and mast cell degeneration.

6. The method of claim 4, wherein the disease is selected from at least one of the group consisting of asthma, allergic rhinitis, allergic conjunctivitis, allergic eczema, atopic dermatitis, acute and chronic urticarias, psoriasis, systemic anaphylaxis, rheumatoid arthritis, osteoarthritis, inflammatory bowel diseases, skin or ocular inflammation and ischemic heart disease.

7. A method of treating a subject suffering from at least one disease selected from the group consisting of an allergic disease and an inflammatory disease comprising administering to the subject in need thereof a therapeutically effective amount of the pharmaceutical composition of claim 3.

8. The method of claim 7, wherein the compound inhibits 5-lipoxgygenase and mast cell degeneration.

9. The method of claim 7, wherein the disease is selected from at least one of the group consisting of asthma, allergic rhinitis, allergic conjunctivitis, allergic eczema, atopic dermatitis, acute and chronic urticarias, psoriasis, systemic anaphylaxis, rheumatoid arthritis, osteoarthritis, inflammatory bowel diseases, skin or ocular inflammation and ischemic heart disease.

10. The method of claim 7, wherein the subject is a mammal.

* * * * *